United States Patent
Young et al.

(10) Patent No.: US 12,054,520 B2
(45) Date of Patent: Aug. 6, 2024

(54) CONTROL OF AND IMAGING TECHNIQUES FOR PROTEIN NANOSCAFFOLDS

(71) Applicant: Board of Trustees of Michigan State University, East Lansing, MI (US)

(72) Inventors: Eric Jeffrey Young, Berkeley, CA (US); Cheryl A. Kerfeld, Melrose, MN (US); Daniel Christopher Ducat, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/531,183

(22) Filed: Nov. 19, 2021

(65) Prior Publication Data

US 2022/0162268 A1    May 26, 2022

Related U.S. Application Data

(60) Provisional application No. 63/116,427, filed on Nov. 20, 2020.

(51) Int. Cl.
*C07K 14/195* (2006.01)
*C12N 15/70* (2006.01)

(52) U.S. Cl.
CPC ............ *C07K 14/195* (2013.01); *C12N 15/70* (2013.01); *C07K 2319/00* (2013.01)

(58) Field of Classification Search
CPC .............. C07K 14/195; C07K 2319/00; C07K 2319/01; C12N 15/70; C12N 15/62
See application file for complete search history.

(56) References Cited

PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Eric Jeffrey Young (On Designing Biological Nanoscale Organization, Ph.D. Thesis, Michigan State University, p. 1-146, 2019). (Year: 2019).*
Sutter et al. Assembly principles and structure of a 6.5-MDa bacterial microcompartment shell. Science (2017), 356: 1293-1297. (Year: 2017).*

* cited by examiner

*Primary Examiner* — Iqbal H Chowdhury
(74) *Attorney, Agent, or Firm* — McKee, Voorhees & Sease, PLC

(57) ABSTRACT

Described herein are constructs, compositions and methods for precise in vivo imaging of the structures and dynamics of protein-based scaffolds with and without their designated cargos.

7 Claims, 14 Drawing Sheets

Specification includes a Sequence Listing.

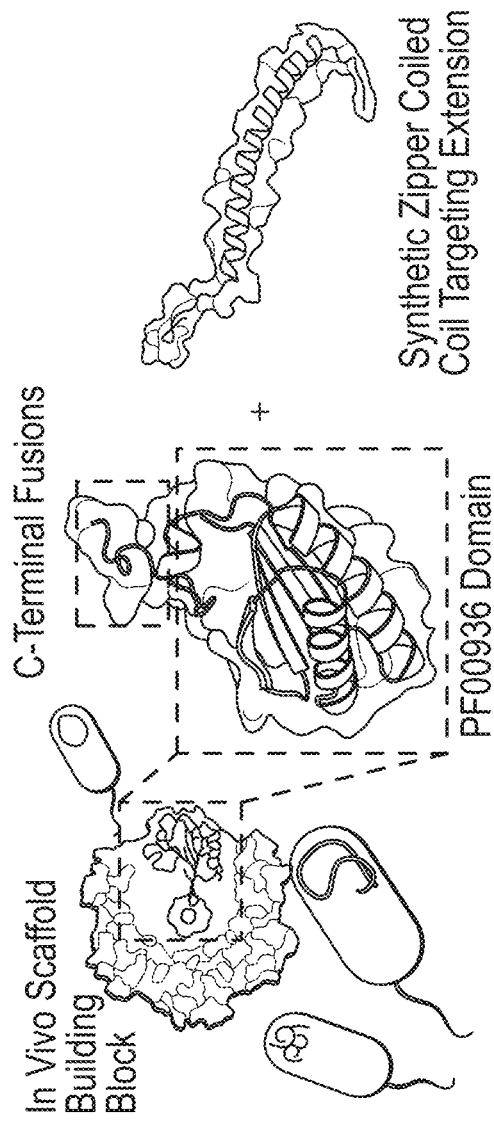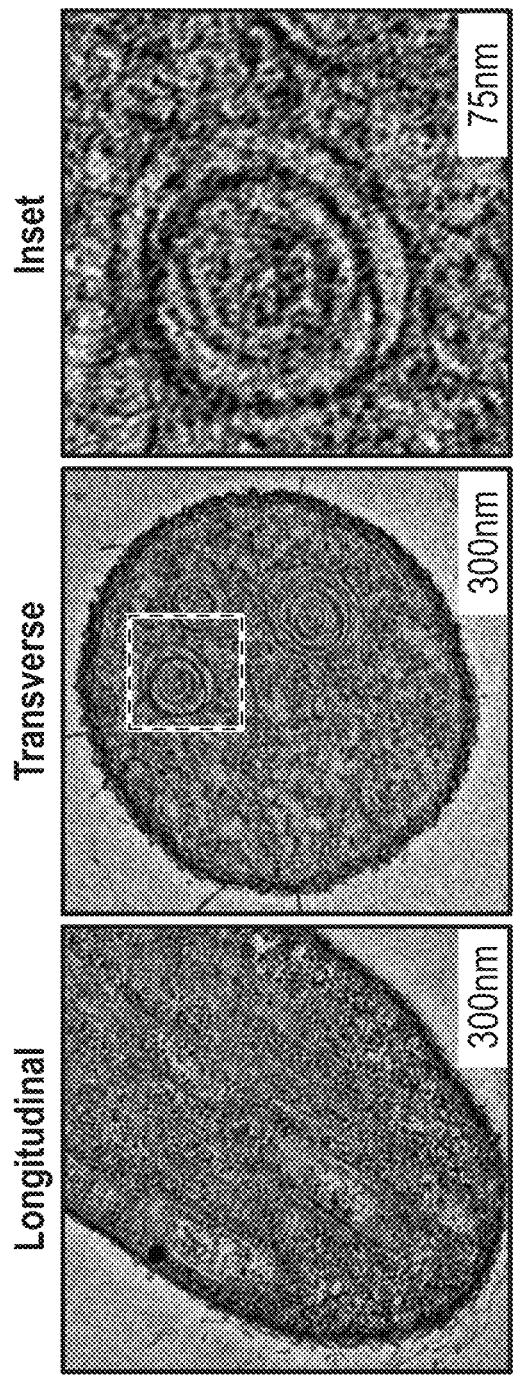
FIG. 1A
FIG. 1B

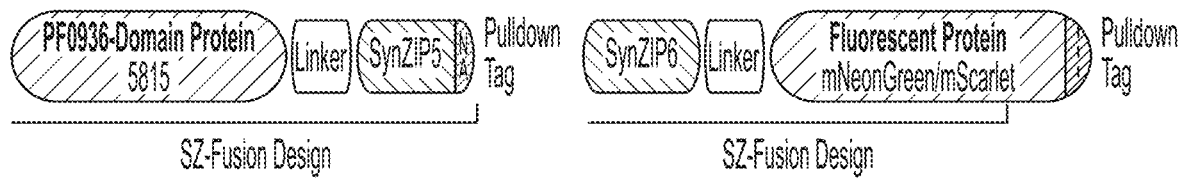
FIG. 1G
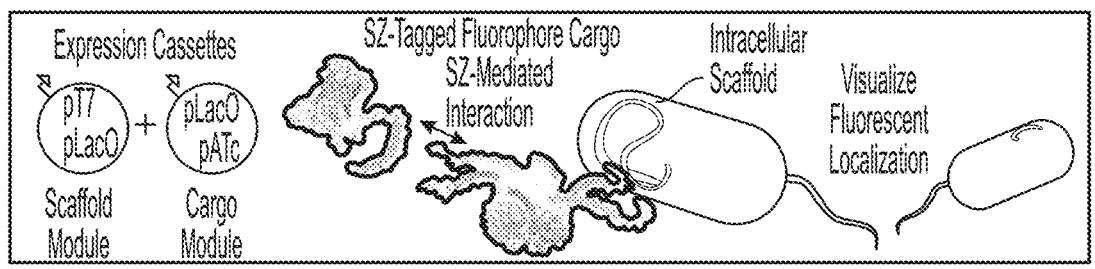
FIG. 2A
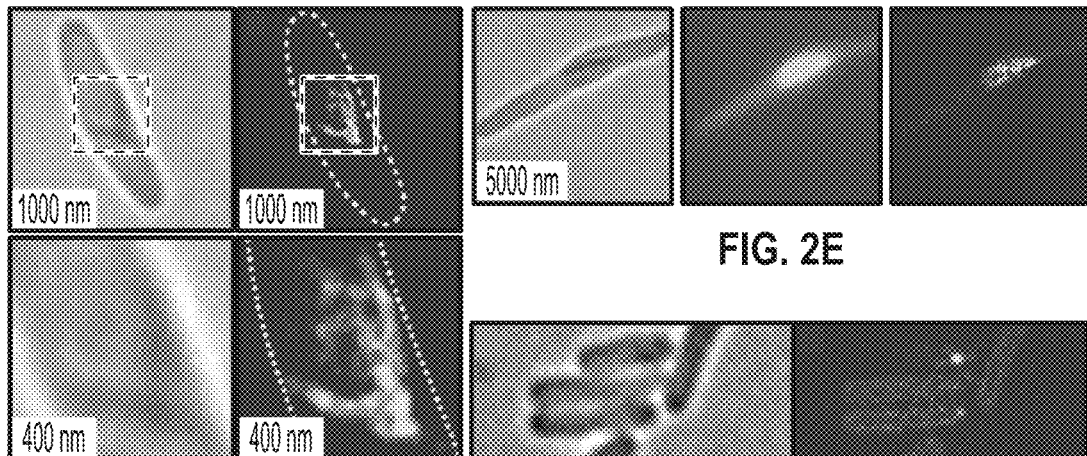
FIG. 2B    FIG. 2C
FIG. 2E
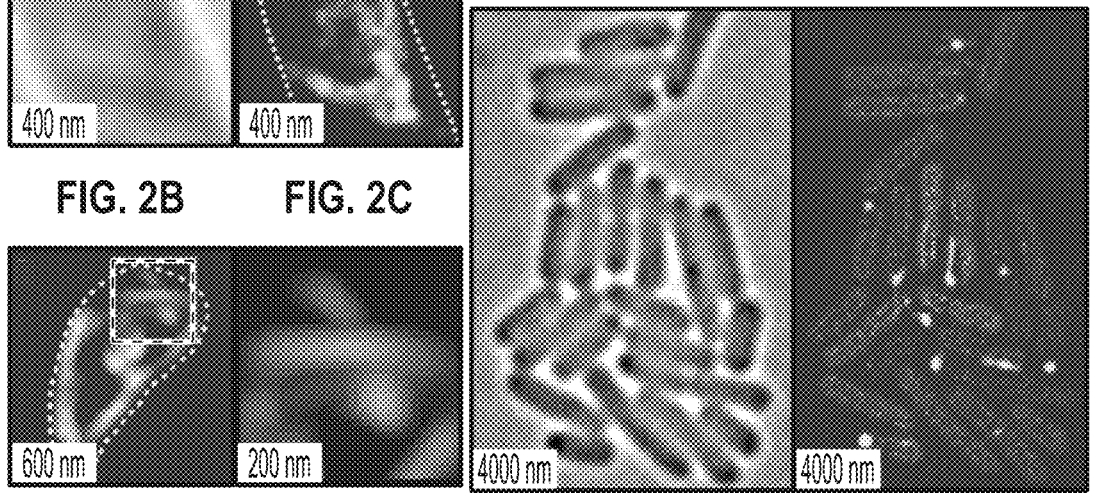
FIG. 2D    FIG. 2F    FIG. 2G

SEQUENCE LISTING

<160> NUMBER OF SEQ ID NOS: 30

<210> SEQ ID NO 1
<211> LENGTH: 99
<212> TYPE: PRT
<213> ORGANISM: Haliangium ochraceum

<400> SEQUENCE: 1

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Tyr Val Thr Ala Val Val Arg Gly
        35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Arg Pro His
65              70                  75                  80

Val Asn Val Asp Ala Ala Leu Pro Leu Gly Arg Thr Pro Gly Met Asp
                85                  90                  95

Lys Ser Ala

<210> SEQ ID NO 2
<211> LENGTH: 99
<212> TYPE: PRT
<213> ORGANISM: Artificial Sequence
<220> FEATURE:
<223> OTHER INFORMATION: A synthetic sequence

<400> SEQUENCE: 2

Met Ala Asp Ala Leu Gly Met Ile Glu Val Arg Gly Phe Val Gly Met
1               5                   10                  15

Val Glu Ala Ala Asp Ala Met Val Lys Ala Ala Val Glu Leu Ile
            20                  25                  30

Gly Tyr Glu Lys Thr Gly Gly Tyr Val Thr Ala Val Val Arg Gly
        35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Arg Pro His
65              70                  75                  80

Val Asn Val Asp Ala Ala Leu Pro Leu Gly Arg Thr Pro Gly Met Asp
                85                  90                  95

Lys Ser Ala

<210> SEQ ID NO 3
<211> LENGTH: 99
<212> TYPE: PRT
<213> ORGANISM: Artificial Sequence
<220> FEATURE:
<223> OTHER INFORMATION: A synthetic sequence

<400> SEQUENCE: 3

Met Ala Asp Ala Leu Gly Met Ile Glu Val Arg Gly Phe Val Gly Met
1               5                   10                  15

Val Glu Ala Ala Asp Ala Met Val Lys Ala Ala Pro Val Glu Leu Ile
            20                  25                  30

Gly Tyr Glu Lys Thr Gly Gly Tyr Val Thr Ala Val Val Arg Gly
        35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Arg Pro His
65              70                  75                  80

Val Asn Val Asp Ala Ala Leu Pro Leu Gly Arg Thr Pro Gly Met Asp
                85                  90                  95

Lys Ser Ala

<210> SEQ ID NO 4
<211> LENGTH: 99
<212> TYPE: PRT
<213> ORGANISM: Artificial Sequence
<220> FEATURE:
<223> OTHER INFORMATION: A synthetic sequence

<400> SEQUENCE: 4

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

Glu Arg Val Gly Glu Val Val Ala Val His Val Ile Pro Ala Pro His
65                  70                  75                  80

Val Asn Val Asp Ala Ala Leu Pro Leu Gly Arg Thr Pro Gly Met Asp
                85                  90                  95

Lys Ser Ala

<210> SEQ ID NO 5
<211> LENGTH: 44
<212> TYPE: PRT
<213> ORGANISM: Artificial Sequence
<220> FEATURE:
<223> OTHER INFORMATION: A synthetic sequence

<400> SEQUENCE: 5

Asn Thr Val Lys Glu Leu Lys Asn Tyr Ile Gln Glu Leu Glu Glu Arg
1               5                   10                  15

Asn Ala Glu Leu Lys Asn Leu Lys Glu His Leu Lys Phe Ala Lys Ala
            20                  25                  30

Glu Leu Glu Phe Glu Leu Ala Ala His Lys Phe Glu
        35                  40

<210> SEQ ID NO 6
<211> LENGTH: 55
<212> TYPE: PRT
<213> ORGANISM: Artificial Sequence
<220> FEATURE:
<223> OTHER INFORMATION: A synthetic sequence

<400> SEQUENCE: 6

Met Gln Lys Val Ala Gln Leu Lys Asn Arg Val Ala Tyr Lys Leu Lys
1               5                   10                  15

Glu Asn Ala Lys Leu Glu Asn Ile Val Ala Arg Leu Glu Asn Asp Asn
            20                  25                  30

Ala Asn Leu Glu Lys Asp Ile Ala Asn Leu Glu Lys Asp Ile Ala Asn
        35                  40                  45

Leu Glu Arg Asp Val Ala Arg
    50                  55

<210> SEQ ID NO 7
<211> LENGTH: 5
<212> TYPE: PRT
<213> ORGANISM: Artificial Sequence
<220> FEATURE:

-continued

<223> OTHER INFORMATION: A synthetic sequence

<400> SEQUENCE: 7

Gly Gly Gly Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: A synthetic sequence

<400> SEQUENCE: 8

Tyr Pro Tyr Asp Val Pro Asp Tyr Ala
1               5

<210> SEQ ID NO 9
<211> LENGTH: 61
<212> TYPE: PRT
<213> ORGANISM: Artificial Sequence
<220> FEATURE:
<223> OTHER INFORMATION: A synthetic sequence

<400> SEQUENCE: 9

Gly Gly Gly Gly Ser Asn Thr Val Lys Glu Leu Lys Asn Tyr Ile Gln
1               5                   10                  15

Glu Leu Glu Glu Arg Asn Ala Glu Leu Lys Asn Leu Lys Glu His Leu
            20                  25                  30

Lys Phe Ala Lys Ala Glu Leu Glu Phe Glu Leu Ala Ala His Lys Phe
        35                  40                  45

Glu Pro Pro Gly Tyr Pro Tyr Asp Val Pro Asp Tyr Ala
    50                  55                  60

<210> SEQ ID NO 10
<211> LENGTH: 160
<212> TYPE: PRT
<213> ORGANISM: Artificial Sequence
<220> FEATURE:
<223> OTHER INFORMATION: A synthetic sequence

<400> SEQUENCE: 10

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala Gly Gly Gly Ser Asn Thr Val Lys Glu Leu Lys Asn
            100                 105                 110

Tyr Ile Gln Glu Leu Glu Glu Arg Asn Ala Glu Leu Lys Asn Leu Lys
        115                 120                 125

Glu His Leu Lys Phe Ala Lys Ala Glu Leu Glu Phe Glu Leu Ala Ala
    130                 135                 140

His Lys Phe Glu Pro Pro Gly Tyr Pro Tyr Asp Val Pro Asp Tyr Ala
145                 150                 155                 160

<210> SEQ ID NO 11
<211> LENGTH: 160
<212> TYPE: PRT
<213> ORGANISM: Artificial Sequence
<220> FEATURE:
<223> OTHER INFORMATION: A synthetic sequence

<400> SEQUENCE: 11

Met Ala Asp Ala Leu Gly Met Ile Glu Val Arg Gly Phe Val Gly Met
1               5                   10                  15

Val Glu Ala Ala Asp Ala Met Val Lys Ala Ala Ala Val Glu Leu Ile
                20                  25                  30

Gly Tyr Glu Lys Thr Gly Gly Gly Tyr Val Thr Ala Val Val Arg Gly
            35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala Gly Gly Gly Ser Asn Thr Val Lys Glu Leu Lys Asn
            100                 105                 110

Tyr Ile Gln Glu Leu Glu Glu Arg Asn Ala Glu Leu Lys Asn Leu Lys
        115                 120                 125

Glu His Leu Lys Phe Ala Lys Ala Glu Leu Glu Phe Glu Leu Ala Ala
130                 135                 140

His Lys Phe Glu Pro Pro Gly Tyr Pro Tyr Asp Val Pro Asp Tyr Ala
145                 150                 155                 160

<210> SEQ ID NO 12
<211> LENGTH: 160
<212> TYPE: PRT
<213> ORGANISM: Artificial Sequence
<220> FEATURE:
<223> OTHER INFORMATION: A synthetic sequence

<400> SEQUENCE: 12

Met Ala Asp Ala Leu Gly Met Ile Glu Val Arg Gly Phe Val Gly Met
1               5                   10                  15

Val Glu Ala Ala Asp Ala Met Val Lys Ala Ala Pro Val Glu Leu Ile
                20                  25                  30

Gly Tyr Glu Lys Thr Gly Gly Gly Tyr Val Thr Ala Val Val Arg Gly
            35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala Gly Gly Gly Ser Asn Thr Val Lys Glu Leu Lys Asn
            100                 105                 110

Tyr Ile Gln Glu Leu Glu Glu Arg Asn Ala Glu Leu Lys Asn Leu Lys
        115                 120                 125

Glu His Leu Lys Phe Ala Lys Ala Glu Leu Glu Phe Glu Leu Ala Ala
130                 135                 140

```
His Lys Phe Glu Pro Pro Gly Tyr Pro Tyr Asp Val Pro Asp Tyr Ala
145                 150                 155                 160

<210> SEQ ID NO 13
<211> LENGTH: 160
<212> TYPE: PRT
<213> ORGANISM: Artificial Sequence
<220> FEATURE:
<223> OTHER INFORMATION: A synthetic sequence

<400> SEQUENCE: 13

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
                20                  25                  30

Gly Tyr Glu Lys Thr Gly Gly Gly Tyr Val Thr Ala Val Val Arg Gly
            35                  40                  45

Asp Val Ala Ala Val Lys Ala Ala Thr Glu Ala Gly Gln Arg Ala Ala
        50                  55                  60

Glu Arg Val Gly Glu Val Val Ala Val His Val Ile Pro Ala Pro His
65                  70                  75                  80

Val Asn Val Asp Ala Ala Leu Pro Leu Gly Arg Thr Pro Gly Met Asp
                85                  90                  95

Lys Ser Ala Gly Gly Gly Ser Asn Thr Val Lys Glu Leu Lys Asn
            100                 105                 110

Tyr Ile Gln Glu Leu Glu Glu Arg Asn Ala Glu Leu Lys Asn Leu Lys
        115                 120                 125

Glu His Leu Lys Phe Ala Lys Ala Glu Leu Glu Phe Glu Leu Ala Ala
    130                 135                 140

His Lys Phe Glu Pro Pro Gly Tyr Pro Tyr Asp Val Pro Asp Tyr Ala
145                 150                 155                 160

<210> SEQ ID NO 14
<211> LENGTH: 10
<212> TYPE: PRT
<213> ORGANISM: Artificial Sequence
<220> FEATURE:
<223> OTHER INFORMATION: A synthetic sequence

<400> SEQUENCE: 14

Gly Ser Gly Gly Gly Ser Gly Gly Gly Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: A synthetic sequence

<400> SEQUENCE: 15

Ser Ala Trp Ser His Pro Gln Phe Glu Lys
1               5                   10

<210> SEQ ID NO 16
<211> LENGTH: 236
<212> TYPE: PRT
<213> ORGANISM: Artificial Sequence
<220> FEATURE:
<223> OTHER INFORMATION: A synthetic sequence

<400> SEQUENCE: 16
```

Met Val Ser Lys Gly Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
            35                  40                  45

Leu Lys Ser Thr Lys Gly Asp Leu Gln Phe Ser Pro Trp Ile Leu Val
50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
            85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
            115                 120                 125

Gly Thr Gly Phe Pro Ala Asp Gly Pro Val Met Thr Asn Ser Leu Thr
            130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
                180                 185                 190

Ala Asn Tyr Leu Lys Asn Gln Pro Met Tyr Val Phe Arg Lys Thr Glu
                195                 200                 205

Leu Lys His Ser Lys Thr Glu Leu Asn Phe Lys Glu Trp Gln Lys Ala
                210                 215                 220

Phe Thr Asp Val Met Gly Met Asp Glu Leu Tyr Lys
225                 230                 235

<210> SEQ ID NO 17
<211> LENGTH: 232
<212> TYPE: PRT
<213> ORGANISM: Artificial Sequence
<220> FEATURE:
<223> OTHER INFORMATION: A synthetic sequence

<400> SEQUENCE: 17

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ser Trp Asp Ile Leu Ser Pro
50                  55                  60

Gln Phe Met Tyr Gly Ser Arg Ala Phe Ile Lys His Pro Ala Asp Ile
65                  70                  75                  80

Pro Asp Tyr Tyr Lys Gln Ser Phe Pro Glu Gly Phe Lys Trp Glu Arg
            85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
            115                 120                 125

```
Asn Phe Pro Pro Asp Gly Pro Val Met Gln Lys Lys Thr Met Gly Trp
        130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
                180                 185                 190

Ala Tyr Asn Val Asp Arg Lys Leu Asp Ile Thr Ser His Asn Glu Asp
            195                 200                 205

Tyr Thr Val Val Glu Gln Tyr Glu Arg Ser Gly Arg His Ser Thr
210                 215                 220

Gly Gly Met Asp Glu Leu Tyr Lys
225                 230

<210> SEQ ID NO 18
<211> LENGTH: 311
<212> TYPE: PRT
<213> ORGANISM: Artificial Sequence
<220> FEATURE:
<223> OTHER INFORMATION: A synthetic sequence

<400> SEQUENCE: 18

Met Gln Lys Val Ala Gln Leu Lys Asn Arg Val Ala Tyr Lys Leu Lys
1               5                   10                  15

Glu Asn Ala Lys Leu Glu Asn Ile Val Ala Arg Leu Glu Asn Asp Asn
            20                  25                  30

Ala Asn Leu Glu Lys Asp Ile Ala Asn Leu Glu Lys Asp Ile Ala Asn
        35                  40                  45

Leu Glu Arg Asp Val Ala Arg Gly Ser Gly Gly Ser Gly Gly Gly
    50                  55                  60

Ser Met Val Ser Lys Gly Glu Glu Asp Asn Met Ala Ser Leu Pro Ala
65                  70                  75                  80

Thr His Glu Leu His Ile Phe Gly Ser Ile Asn Gly Val Asp Phe Asp
                85                  90                  95

Met Val Gly Gln Gly Thr Gly Asn Pro Asn Asp Gly Tyr Glu Glu Leu
            100                 105                 110

Asn Leu Lys Ser Thr Lys Gly Asp Leu Gln Phe Ser Pro Trp Ile Leu
        115                 120                 125

Val Pro His Ile Gly Tyr Gly Phe His Gln Tyr Leu Pro Tyr Pro Asp
    130                 135                 140

Gly Met Ser Pro Phe Gln Ala Ala Met Val Asp Gly Ser Gly Tyr Gln
145                 150                 155                 160

Val His Arg Thr Met Gln Phe Glu Asp Gly Ala Ser Leu Thr Val Asn
                165                 170                 175

Tyr Arg Tyr Thr Tyr Glu Gly Ser His Ile Lys Gly Glu Ala Gln Val
            180                 185                 190

Lys Gly Thr Gly Phe Pro Ala Asp Gly Pro Val Met Thr Asn Ser Leu
        195                 200                 205

Thr Ala Ala Asp Trp Cys Arg Ser Lys Lys Thr Tyr Pro Asn Asp Lys
    210                 215                 220

Thr Ile Ile Ser Thr Phe Lys Trp Ser Tyr Thr Thr Gly Asn Gly Lys
225                 230                 235                 240

Arg Tyr Arg Ser Thr Ala Arg Thr Thr Tyr Thr Phe Ala Lys Pro Met
                245                 250                 255
```

```
Ala Ala Asn Tyr Leu Lys Asn Gln Pro Met Tyr Val Phe Arg Lys Thr
            260                 265                 270

Glu Leu Lys His Ser Lys Thr Glu Leu Asn Phe Lys Glu Trp Gln Lys
        275                 280                 285

Ala Phe Thr Asp Val Met Gly Met Asp Glu Leu Tyr Lys Ser Ala Trp
    290                 295                 300

Ser His Pro Gln Phe Glu Lys
305                 310

<210> SEQ ID NO 19
<211> LENGTH: 307
<212> TYPE: PRT
<213> ORGANISM: Artificial Sequence
<220> FEATURE:
<223> OTHER INFORMATION: A synthetic sequence

<400> SEQUENCE: 19

Met Gln Lys Val Ala Gln Leu Lys Asn Arg Val Ala Tyr Lys Leu Lys
1               5                   10                  15

Glu Asn Ala Lys Leu Glu Asn Ile Val Ala Arg Leu Glu Asn Asp Asn
            20                  25                  30

Ala Asn Leu Glu Lys Asp Ile Ala Asn Leu Glu Lys Asp Ile Ala Asn
        35                  40                  45

Leu Glu Arg Asp Val Ala Arg Gly Ser Gly Gly Ser Gly Gly Gly Gly
    50                  55                  60

Ser Met Val Ser Lys Gly Glu Ala Val Ile Lys Glu Phe Met Arg Phe
65                  70                  75                  80

Lys Val His Met Glu Gly Ser Met Asn Gly His Glu Phe Glu Ile Glu
                85                  90                  95

Gly Glu Gly Glu Gly Arg Pro Tyr Glu Gly Thr Gln Thr Ala Lys Leu
            100                 105                 110

Lys Val Thr Lys Gly Gly Pro Leu Pro Phe Ser Trp Asp Ile Leu Ser
        115                 120                 125

Pro Gln Phe Met Tyr Gly Ser Arg Ala Phe Ile Lys His Pro Ala Asp
    130                 135                 140

Ile Pro Asp Tyr Tyr Lys Gln Ser Phe Pro Glu Gly Phe Lys Trp Glu
145                 150                 155                 160

Arg Val Met Asn Phe Glu Asp Gly Gly Ala Val Thr Val Thr Gln Asp
                165                 170                 175

Thr Ser Leu Glu Asp Gly Thr Leu Ile Tyr Lys Val Lys Leu Arg Gly
            180                 185                 190

Thr Asn Phe Pro Pro Asp Gly Pro Val Met Gln Lys Lys Thr Met Gly
        195                 200                 205

Trp Glu Ala Ser Thr Glu Arg Leu Tyr Pro Glu Asp Gly Val Leu Lys
    210                 215                 220

Gly Asp Ile Lys Met Ala Leu Arg Leu Lys Asp Gly Gly Arg Tyr Leu
225                 230                 235                 240

Ala Asp Phe Lys Thr Thr Tyr Lys Ala Lys Lys Pro Val Gln Met Pro
                245                 250                 255

Gly Ala Tyr Asn Val Asp Arg Lys Leu Asp Ile Thr Ser His Asn Glu
            260                 265                 270

Asp Tyr Thr Val Val Glu Gln Tyr Glu Arg Ser Glu Gly Arg His Ser
        275                 280                 285

Thr Gly Gly Met Asp Glu Leu Tyr Lys Ser Ala Trp Ser His Pro Gln
    290                 295                 300
```

Phe Glu Lys
305

<210> SEQ ID NO 20
<211> LENGTH: 276
<212> TYPE: PRT
<213> ORGANISM: Synechococcus elongatus

<400> SEQUENCE: 20

Met Ser Ala Ser Leu Pro Ala Tyr Ser Gln Pro Arg Asn Ala Gly Ala
1               5                   10                  15

Leu Gly Val Ile Cys Thr Arg Ser Phe Pro Ala Val Val Gly Thr Ala
            20                  25                  30

Asp Met Met Leu Lys Ser Ala Asp Val Thr Leu Ile Gly Tyr Glu Lys
        35                  40                  45

Thr Gly Ser Gly Phe Cys Thr Ala Ile Ile Arg Gly Gly Tyr Ala Asp
    50                  55                  60

Ile Lys Leu Ala Leu Glu Ala Gly Val Ala Thr Ala Arg Gln Phe Glu
65                  70                  75                  80

Gln Tyr Val Ser Ser Thr Ile Leu Pro Arg Pro Gln Gly Asn Leu Glu
                85                  90                  95

Ala Val Leu Pro Ile Ser Arg Arg Leu Ser Gln Glu Ala Met Ala Thr
            100                 105                 110

Arg Ser His Gln Asn Val Gly Ala Ile Gly Leu Ile Glu Thr Asn Gly
        115                 120                 125

Phe Pro Ala Leu Val Gly Ala Ala Asp Ala Met Leu Lys Ser Ala Asn
    130                 135                 140

Val Lys Leu Ile Cys Tyr Glu Lys Thr Gly Ser Gly Leu Cys Thr Ala
145                 150                 155                 160

Ile Val Gln Gly Thr Val Ser Asn Val Thr Val Ala Val Glu Ala Gly
                165                 170                 175

Met Tyr Ala Ala Glu Arg Ile Gly Gln Leu Asn Ala Ile Met Val Ile
            180                 185                 190

Pro Arg Pro Leu Asp Asp Leu Met Asp Ser Leu Pro Glu Pro Gln Ser
        195                 200                 205

Asp Ser Glu Ala Ala Gln Pro Leu Gln Leu Pro Leu Arg Val Arg Glu
    210                 215                 220

Lys Gln Pro Leu Leu Glu Leu Pro Glu Leu Glu Arg Gln Pro Ile Ala
225                 230                 235                 240

Ile Glu Ala Pro Arg Leu Leu Ala Glu Glu Arg Gln Ser Ala Leu Glu
                245                 250                 255

Leu Ala Gln Glu Thr Pro Leu Ala Glu Pro Leu Glu Leu Pro Asn Pro
            260                 265                 270

Arg Asp Asp Gln
        275

<210> SEQ ID NO 21
<211> LENGTH: 138
<212> TYPE: PRT
<213> ORGANISM: Synechococcus BMC

<400> SEQUENCE: 21

Met Leu Lys Ser Ala Asn Val Lys Leu Ile Cys Tyr Glu Lys Thr Gly
1               5                   10                  15

Ser Gly Leu Cys Thr Ala Ile Val Gln Gly Thr Val Ser Asn Val Thr
            20                  25                  30

Val Ala Val Glu Ala Gly Met Tyr Ala Ala Glu Arg Ile Gly Gln Leu
            35                  40                  45

Asn Ala Ile Met Val Ile Pro Arg Pro Leu Asp Asp Leu Met Asp Ser
        50                  55                  60

Leu Pro Glu Pro Gln Ser Asp Ser Glu Ala Ala Gln Pro Leu Gln Leu
65                  70                  75                  80

Pro Leu Arg Val Arg Glu Lys Gln Pro Leu Leu Glu Leu Pro Glu Leu
                85                  90                  95

Glu Arg Gln Pro Ile Ala Ile Glu Ala Pro Arg Leu Leu Ala Glu Glu
            100                 105                 110

Arg Gln Ser Ala Leu Glu Leu Ala Gln Glu Thr Pro Leu Ala Glu Pro
        115                 120                 125

Leu Glu Leu Pro Asn Pro Arg Asp Asp Gln
    130                 135

<210> SEQ ID NO 22
<211> LENGTH: 276
<212> TYPE: PRT
<213> ORGANISM: Synechococcus elongatus

<400> SEQUENCE: 22

Met Ser Ala Ser Leu Pro Ala Tyr Ser Gln Pro Arg Asn Ala Gly Ala
1               5                   10                  15

Leu Gly Val Ile Cys Thr Arg Ser Phe Pro Ala Val Val Gly Thr Ala
                20                  25                  30

Asp Met Met Leu Lys Ser Ala Asp Val Thr Leu Ile Gly Tyr Glu Lys
            35                  40                  45

Thr Gly Ser Gly Phe Cys Thr Ala Ile Ile Arg Gly Gly Tyr Ala Asp
        50                  55                  60

Ile Lys Leu Ala Leu Glu Ala Gly Val Ala Thr Ala Arg Gln Phe Glu
65                  70                  75                  80

Gln Tyr Val Ser Ser Thr Ile Leu Pro Arg Pro Gln Gly Asn Leu Glu
                85                  90                  95

Ala Val Leu Pro Ile Ser Arg Arg Leu Ser Gln Glu Ala Met Ala Thr
            100                 105                 110

Arg Ser His Gln Asn Val Gly Ala Ile Gly Leu Ile Glu Thr Asn Gly
        115                 120                 125

Phe Pro Ala Leu Val Gly Ala Ala Asp Ala Met Leu Lys Ser Ala Asn
    130                 135                 140

Val Lys Leu Ile Cys Tyr Glu Lys Thr Gly Ser Gly Leu Cys Thr Ala
145                 150                 155                 160

Ile Val Gln Gly Thr Val Ser Asn Val Thr Val Ala Val Glu Ala Gly
                165                 170                 175

Met Tyr Ala Ala Glu Arg Ile Gly Gln Leu Asn Ala Ile Met Val Ile
            180                 185                 190

Pro Arg Pro Leu Asp Asp Leu Met Asp Ser Leu Pro Glu Pro Gln Ser
        195                 200                 205

Asp Ser Glu Ala Ala Gln Pro Leu Gln Leu Pro Leu Arg Val Arg Glu
    210                 215                 220

Lys Gln Pro Leu Leu Glu Leu Pro Glu Leu Arg Gln Pro Ile Ala
225                 230                 235                 240

Ile Glu Ala Pro Arg Leu Leu Ala Glu Glu Arg Gln Ser Ala Leu Glu
                245                 250                 255

Leu Ala Gln Glu Thr Pro Leu Ala Glu Pro Leu Glu Leu Pro Asn Pro

Arg Asp Asp Gln
        275

<210> SEQ ID NO 23
<211> LENGTH: 102
<212> TYPE: PRT
<213> ORGANISM: Synechococcus elongatus

<400> SEQUENCE: 23

Met Pro Ile Ala Val Gly Met Ile Glu Thr Leu Gly Phe Pro Ala Val
1               5                   10                  15

Val Glu Ala Ala Asp Ala Met Val Lys Ala Ala Arg Val Thr Leu Val
            20                  25                  30

Gly Tyr Glu Lys Ile Gly Ser Gly Arg Val Thr Val Ile Val Arg Gly
        35                  40                  45

Asp Val Ser Glu Val Gln Ala Ser Val Ser Ala Gly Leu Asp Ser Ala
    50                  55                  60

Lys Arg Val Ala Gly Gly Glu Val Leu Ser His His Ile Ile Ala Arg
65                  70                  75                  80

Pro His Glu Asn Leu Glu Tyr Val Leu Pro Ile Arg Tyr Thr Glu Ala
                85                  90                  95

Val Glu Gln Phe Arg Met
        100

<210> SEQ ID NO 24
<211> LENGTH: 138
<212> TYPE: PRT
<213> ORGANISM: Synecococcous elongatus

<400> SEQUENCE: 24

Met Ser Ala Ser Leu Pro Ala Tyr Ser Gln Pro Arg Asn Ala Gly Ala
1               5                   10                  15

Leu Gly Val Ile Cys Thr Arg Ser Phe Pro Ala Val Val Gly Thr Ala
            20                  25                  30

Asp Met Met Leu Lys Ser Ala Asp Val Thr Leu Ile Gly Tyr Glu Lys
        35                  40                  45

Thr Gly Ser Gly Phe Cys Thr Ala Ile Ile Arg Gly Gly Tyr Ala Asp
    50                  55                  60

Ile Lys Leu Ala Leu Glu Ala Gly Val Ala Thr Ala Arg Gln Phe Glu
65                  70                  75                  80

Gln Tyr Val Ser Ser Thr Ile Leu Pro Arg Pro Gln Gly Asn Leu Glu
                85                  90                  95

Ala Val Leu Pro Ile Ser Arg Arg Leu Ser Gln Glu Ala Met Ala Thr
            100                 105                 110

Arg Ser His Gln Asn Val Gly Ala Ile Gly Leu Ile Glu Thr Asn Gly
        115                 120                 125

Phe Pro Ala Leu Val Gly Ala Ala Asp Ala
    130                 135

<210> SEQ ID NO 25
<211> LENGTH: 138
<212> TYPE: PRT
<213> ORGANISM: Synecococcus elongatus

<400> SEQUENCE: 25

Met Leu Lys Ser Ala Asn Val Lys Leu Ile Cys Tyr Glu Lys Thr Gly
1               5                   10                  15

```
Ser Gly Leu Cys Thr Ala Ile Val Gln Gly Thr Val Ser Asn Val Thr
        20                  25                  30

Val Ala Val Glu Ala Gly Met Tyr Ala Ala Glu Arg Ile Gly Gln Leu
        35                  40                  45

Asn Ala Ile Met Val Ile Pro Arg Pro Leu Asp Asp Leu Met Asp Ser
 50                  55                  60

Leu Pro Glu Pro Gln Ser Asp Ser Glu Ala Ala Gln Pro Leu Gln Leu
 65                  70                  75                  80

Pro Leu Arg Val Arg Glu Lys Gln Pro Leu Leu Glu Leu Pro Glu Leu
                85                  90                  95

Glu Arg Gln Pro Ile Ala Ile Glu Ala Pro Arg Leu Leu Ala Glu Glu
                100                 105                 110

Arg Gln Ser Ala Leu Glu Leu Ala Gln Glu Thr Pro Leu Ala Glu Pro
            115                 120                 125

Leu Glu Leu Pro Asn Pro Arg Asp Asp Gln
        130                 135

<210> SEQ ID NO 26
<211> LENGTH: 113
<212> TYPE: PRT
<213> ORGANISM: Halothece sp

<400> SEQUENCE: 26

Met Ala Val Ala Val Gly Met Ile Glu Thr Leu Gly Phe Pro Ala Val
1               5                   10                  15

Val Glu Ala Ala Asp Ala Met Val Lys Ala Ala Arg Val Thr Leu Val
            20                  25                  30

Gly Tyr Glu Lys Ile Gly Thr Gly Arg Val Thr Val Ile Val Arg Gly
        35                  40                  45

Asp Val Ser Glu Val Gln Ala Ser Val Ser Ala Gly Thr Glu Ser Val
 50                  55                  60

Lys Arg Val Asn Gly Gly Gln Val Leu Ser Thr His Ile Ile Ala Arg
 65                  70                  75                  80

Pro His Glu Asn Leu Glu Tyr Val Leu Pro Ile Arg Tyr Thr Glu Glu
                85                  90                  95

Val Glu Gln Phe Arg Glu Gly Val Gly Thr Pro Arg Asn Ile Thr Arg
                100                 105                 110

Gln

<210> SEQ ID NO 27
<211> LENGTH: 101
<212> TYPE: PRT
<213> ORGANISM: Halothece sp

<400> SEQUENCE: 27

Met Pro Ile Ala Val Gly Met Ile Glu Thr Leu Gly Phe Pro Ala Val
1               5                   10                  15

Val Glu Ala Ala Asp Ala Met Val Lys Ala Ala Arg Val Thr Leu Val
            20                  25                  30

Gly Tyr Glu Lys Ile Gly Thr Gly Arg Val Thr Val Ile Val Arg Gly
        35                  40                  45

Asp Val Ser Glu Val Gln Ala Ser Val Ser Ala Gly Val Asp Ser Ala
 50                  55                  60

Asn Arg Val Asn Gly Gly Glu Val Leu Ser Thr His Ile Ile Ala Arg
 65                  70                  75                  80
```

Pro His Glu Asn Leu Glu Tyr Val Leu Pro Ile Arg Tyr Thr Glu Ala
                85                  90                  95

Val Glu Gln Phe Arg
            100

<210> SEQ ID NO 28
<211> LENGTH: 93
<212> TYPE: PRT
<213> ORGANISM: Mycobacterium smegmatis

<400> SEQUENCE: 28

Met Ser Ser Asn Ala Ile Gly Leu Ile Glu Thr Lys Gly Tyr Val Ala
1               5                   10                  15

Ala Leu Ala Ala Ala Asp Ala Met Val Lys Ala Ala Asn Val Thr Ile
            20                  25                  30

Thr Asp Arg Gln Gln Val Gly Asp Gly Leu Val Ala Val Ile Val Thr
        35                  40                  45

Gly Glu Val Gly Ala Val Lys Ala Ala Thr Glu Ala Gly Ala Glu Thr
    50                  55                  60

Ala Ser Gln Val Gly Glu Leu Val Ser Val His Val Ile Pro Arg Pro
65                  70                  75                  80

His Ser Glu Leu Gly Ala His Phe Ser Val Ser Ser Lys
                85                  90

<210> SEQ ID NO 29
<211> LENGTH: 99
<212> TYPE: PRT
<213> ORGANISM: Citrobacter freundii

<400> SEQUENCE: 29

Met Gln Gln Glu Ala Leu Gly Met Val Glu Thr Lys Gly Leu Thr Ala
1               5                   10                  15

Ala Ile Glu Ala Ala Asp Ala Met Val Lys Ser Ala Asn Val Met Leu
            20                  25                  30

Val Gly Tyr Glu Lys Ile Gly Ser Gly Leu Val Thr Val Ile Val Arg
        35                  40                  45

Gly Asp Val Gly Ala Val Lys Ala Ala Thr Asp Ala Gly Ala Ala Ala
    50                  55                  60

Ala Arg Asn Val Gly Glu Val Lys Ala Val His Val Ile Pro Arg Pro
65                  70                  75                  80

His Thr Asp Val Glu Lys Ile Leu Pro Lys Gly Ile Arg Leu Val Lys
                85                  90                  95

Asp Pro Ala

<210> SEQ ID NO 30
<211> LENGTH: 99
<212> TYPE: PRT
<213> ORGANISM: Haliangium ochraceum

<400> SEQUENCE: 30

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

```
Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala
```

CONTROL OF AND IMAGING TECHNIQUES FOR PROTEIN NANOSCAFFOLDS

This application claims benefit of priority to the filing date of U.S. Provisional Application Ser. No. 63/116,427, filed Nov. 20, 2020, the contents of which are specifically incorporated herein by reference in their entity.

STATEMENT OF GOVERNMENT SUPPORT

This invention was made with government support under DE-FG02-91ER20021 awarded by the U.S. Department of Energy. The government has certain rights in the invention.

BACKGROUND

The efficiency of many cellular processes relies on the colocalization of related cellular functions within a shared subcellular space-time (e.g. organelles and ribosomes). Synthetic biologists would like to harness subcellular organization strategies to improve the performance of rationally designed circuits and pathways. For example, improved bioproduct yields could be achieved if the cellular burdens of making such bioproducts via heterologous cellular pathways were reduced, for example, by sequestering the biological machinery and the products of those biological machines within intracellular nanoscaffolds or compartments. However, a number of problems remain before protein nanoscaffolds become commercially useful, such as: identifying the structures of in vivo protein scaffolds at sufficient resolution; controlling the assembly, dynamics, and positioning of scaffolds inside cells; and organizing cellular function on the surface of or within scaffolds in a predictable manner.

SUMMARY

Described herein are constructs, compositions and methods for precise in vivo formation (e.g., and imaging) of the structures and dynamics of protein-based scaffolds with or without their designated cargos. Such constructs, compositions and methods can temporally control protein scaffold and cargo molecule expression, including reporter molecules for high-resolution imaging of the assembly process. The constructs include unique structural components that facilitate scaffold assembly and cargo protein recruitment. By controlling the expression of the scaffolding construct and timing the expression of cargo proteins, optimal scaffold-cargo protein assemblies are achieved.

Currently available methods do not employ the combination of components described herein and typically rely on high-expression promoters (for example, T7 promoters), which are ill-suited for scaffolding applications because high expression of bacterial microcompartment (BMC) shell proteins harms physiology, deforms cell morphology, inhibits division, and promotes untimely cell death. In addition, the leaky expression and non-tunability typical of high-expression promoters complicates proper assembly and the analysis of initial scaffold assembly.

Described herein are fusion proteins that can include (a) a pfam00936 domain (ScaF) linked to a first synthetic zipper domain via a flexible peptide linker; or (b) a cargo protein linked to a second synthetic zipper domain via a flexible linker. Such flexible peptide linkers can be peptides of about 3 to 20 amino acids, with at least 60%, at least 70%, at least 80%, at least 90%, or at least 95% glycine residues, serine residues, or a combination of glycine and serine residues.

Also described herein are expression systems that can include at least one or at least two expression cassettes, wherein a first expression cassette or vector includes a first promoter operably linked to a nucleic acid segment encoding one or more pfam00936 domain (ScaF), each pfam00936 domain (ScaF) fused in frame to a first synthetic zipper domain via a flexible peptide linker; wherein a second expression cassette or vector comprising a promoter operably linked one or more cargo proteins, each cargo protein fused in frame to a second synthetic zipper domain via a flexible linker, or a combination of the first expression cassette and the second expression cassette. For example, at least one of the cargo proteins can be a fluorescent protein. The first promoter, the second promoter, or both promoters can be tunable promoters or inducible promoters. Examples of tunable promoters or inducible promoters that can be used include tetracycline-regulated promoters, propionate-regulated promoters, arabinose-inducible promoters, propionate-inducible promoters, lactose-inducible promoters, or IPTG-inducible promoters.

Also described herein are host cells that can include the pfam00936 domain (ScaF) linked to a first synthetic zipper domain via a flexible peptide linker, fusion proteins that include such ScaF domains, and expression systems therefor. The host cells can be prokaryotic cells or eukaryotic cells. For example, the host cells can be bacterial cells, cyanobacterial cells, yeast cells, insect cells, bird cells, or mammalian cells.

Also described herein are methods that can include transforming a host cell with an expression system comprising at least one or two expression cassettes, wherein a first expression cassette or vector comprises a first promoter operably linked to a nucleic acid segment encoding one or more pfam00936 domain (ScaF), each pfam00936 domain (ScaF) fused in frame to a first synthetic zipper domain via a flexible peptide linker; a second expression cassette or vector comprising a promoter operably linked one or more cargo proteins, each cargo protein fused in frame to a second synthetic zipper domain via a flexible linker; or a combination of the first expression cassette and the second expression cassette.

Kits and in vitro expression/translation systems are also described herein.

DESCRIPTION OF THE FIGURES

FIG. 1A-1G illustrates interaction of a Synthetic Zipper protein-protein interaction domain with an *Haliangium ochraceum* (HO) BMC-H 5815 (referred to as a HO BMC-H) scaffold (ScaFS). FIG. 1A is a schematic of ScaFS building block and the attachment of a C-terminal zipper (SZ) coiled-coil. The C-terminus of a wild type scaffold protein can be the attachment site. In some cases, the C-terminus of the wild type scaffold protein is trimmed before fusion to the zipper. FIG. 1B shows representative transmission electron microscopy (TEM) images of intracellular assemblies formed by overexpression of unmodified HO BMC-H (WT HO 5815 BMC-H). FIG. 1C shows representative TEM images of the HO BMC-H ScaFS bearing a C-terminal Synthetic Zipper (SZ5) domain attached via a proline-rich (rigid; PPG) linker. FIG. 1D shows representative TEM images as in FIG. 1C, except where the linker region is composed of glycine-serine residues (flexible linker; 5815ggsSZ5 construct). Scale bar (white) provides the indicated sizes. FIG. JE illustrates higher-order protein assemblies formed from candidate ScaFs heterologously overexpressed in *E. coli* and imaged with TEM thin section microscopy. For Ho-BMC-H (and respective amino acid point substitutions) a representative longitudinal and transverse section appears shown. For protein sequences see the Detailed Description and Example 2. FIG. 1F further illustrates higher-order intracellular architectures formed by ScaFS bearing a C-terminal SZ5 domain attached via a flexible linker. Representative TEM images of E. coli cells overexpressing modified HO-BMC-H ScaFs, including expression of the K28A modified ScaFs are shown in the top row, expression of the K28P modified ScaFs is shown in the second row, and expression of the R78A modified ScaFs is shown in the third row. The ScaFs were tagged with a C-terminal SZ5 domain via a glycine-serine linker. As illustrated, these ScaFS retain higher-order assembly features compared to those observed when their unmodified parental constructs are overexpressed (see. e.g., FIG. 1A-1B, 1E-1F, bottom). FIG. 1G is a schematic diagram of a Synthetic Zipper-Scaffold (ScaF) protein construct and of a Synthetic Zipper Fluorescent cargo protein construct.

FIG. 2A-2I illustrates cargo protein recruitment to designer intracellular protein scaffolds. FIG. 2A is a schematic illustrating that co-expression of SZ6 fluorophore cargo module and the SZ5-ScaFS scaffolds recruits the fluorescent cargo to the scaffolds. FIG. 2B top panel shows representative filamentous diffracting bodies observed 2 hours following expression of PT7::K28AHO BMC-H-SZ5 (50 μM IPTG) while the bottom panel shows a magnified view of boxed portion of the top panel. FIG. 2C shows the deconvolved localization pattern of the cargo protein PLacO::SZ6-mNeonGreen when co-expressed with the SZ5-ScaFS scaffolding protein describe in FIG. 2B, demonstrating cargo co-localization to fine filamentous features. FIG. 2D shows representative three-dimensional Secondary Ion Mass Spectrometry (3D-SIM) images of cargo-scaffold localization as in FIG. 2C; illustrating that the fluorescent structures form sheets or ribbons similar to those observed by TEM. FIG. 2E shows representative images illustrating localization of an untagged cargo construct, PLacO::mNeonGreen (expression induced by 50 M IPTG) in a cell exhibiting a K28AHO BMC-H-SZ5 diffracting body (left), with unprocessed (center), and deconvolved (right) fluorescence images of the cargo. FIG. 2F shows representative brightfield images 3 hours following expression of PLacO::K28AHO BMC-H-SZ5 (100 μM IPTG) and PaTC::SZ6-mScarlet-I (5 nM anhydrotetracycline (aTc)). FIG. 2G shows representative images of Super-Resolution Radial Fluctuations (SRRF)-processed fluorescence of the same field as in FIG. 2F, 3 hours following expression of PLacO::K28AHO BMC-H-SZ5 (100 μM IPTG) and PaTC::SZ6-mScarlet-I (5 nM aTc). Scale bars as indicated. FIG. 2H shows representative E. coli cells co-expressing a SZ5-tagged ScaF scaffold protein and fluorescent cargo proteins with or without the SZ6 tag. The left six panels show images of cells co-expressing the SZ6-mNeonGreen fluorescent cargo protein without the SZ5-tagged ScaF, while the middle six panels show images of cells co-expressing the SZ5-tagged ScaF with the SZ6-mNeonGreen fluorescent cargo protein. As shown, localized fluorescence is detected when the fluorescent cargo protein is linked to the SZ6 tag, so that it can bind to the SZ5 tag on the ScaF scaffold. The right six panels show images of cells that co-express the SZ5-tagged ScaF scaffold protein with the mNeonGreen fluorescent cargo protein that does not have the SZ6 tag. FIG. 2I illustrates co-localization of alternative cargo molecules to compatible ScaFS-induced intracellular protein assemblies. Representative panels of the localization pattern for untagged cargo (mScarlet-I, left 24 panels) and SZ-tagged cargo (SZ6-mScarlet-I, right 24 panels) when co-expressed in the same type of cells with the K28AHO-BMC-HggsSZ5 scaffold protein. IPTG concentration was modulated to provide scaffolding K28AHO-BMC-HggsSZ5 expression at low induction levels (100 μM IPTG; top 24 panels) or high induction levels (500 μM IPTG; bottom 24 panels). Untagged cargo remained delocalized throughout the cytosol, while compatibly tagged cargo co-localizes with the K28AMHO-BMC-HggsSZ5-induced diffracting bodies. Scale bars as indicated.

FIG. 3A shows cellular images and three dimensional-total internal reflectance microscopy (3D-TIRF) microscopy max intensity projections of cargo (PaTc::SZ6-mNG) following induction of a compatible ScaFS (PLacO::K28AHO BMC-HggsSZ5). Representative frames are displayed for each minute following induction (at time=0); appearance of cargo puncta is indicated by arrowheads. Enlarged image: highlights two fluorescent foci and reference regions within the cell (circles). FIG. 3B graphically illustrates fluorescent intensity measurements of the two fluorescent foci and reference regions within the cell (circles) identified in the enlarged image of FIG. 3A. These foci and reference regions were monitored to track the fluorescence kinetics associated with the recruitment of cargo at newly nucleated scaffold assemblies. FIG. 3C shows additional 3D-TIRF microscopy of targeted cargo (PaTc::SZ6-mNeonGreen) in a field of cells following induction of a compatible ScaFS (PLacO::K28AHO BMC-H ggSZ5). Individual scaffold puncta were identified upon first indication of nucleation (arrowheads; numbers). FIG. 3D graphically illustrates the fluorescence intensity tracked over time (top lines) for the numbered scaffold punta identified in FIG. 3C. Reference areas of background fluorescence are indicated as light grey traces (lower traces). [IPTG=250 μM, anhydrotetracycline (aTc)=5 nM].

FIG. 4A shows a representative series of nucleation events recoded over time in a live E. coli cell as in FIG. 3A but analyzed via Super-Resolution Radial Fluctuations (SRRF). Three foci appear nucleated during the observation period, although only 2 persist throughout the time course. FIG. 4B shows Kymograph of cargo foci position over time. Larger foci remain relatively fixed in position, while small foci exhibit more dynamic repositioning. FIG. 4C shows a schematic of scaffold-cargo reorganization in vivo. Expression leads to the buildup of subunits in the cytosol, eventually triggering the formation of numerous assemblies. Nucleated scaffolds expand rapidly and deplete the cytosolic pool of subunits. Over time, inter-scaffold competition leads to the domination of 1-2 large assemblies and the disassembly of other scaffolds within the cell. FIG. 4D-4E illustrate intracellular cargo dynamics with visualization by SRRF-processing. FIG. 4D shows representative time lapse of a cell expressing SZ6-mNeonGreen and induced to express K28AHO-BMC-HggsSZ5 after t=0. Two clusters of cargo appear to form (bright white and faint white arrowheads). The first focus forms at 7 minutes (bright white arrowhead) and rapidly increases in size and intensity. A second focus forms at 12 minutes (faint white arrowhead) and transiently becomes brighter, before becoming increasingly difficult to resolve. FIG. 4E shows images of the unprocessed fluorescence from the time series shown in FIG. 4D, with 3D-TIRF max intensity projection. Scale bars as indicated.

FIG. 5A schematically illustrates the materials and some of the steps for generating nanoscaffolds. FIG. 5B schematically illustrates methods for improved image reconstruction and visualization of nanoscaffold formation. Such materials and methods can optimize analysis so that optimal types and expression levels of scaffolding proteins and cargo protein are selected so the process of scaffold formation can be optimized.

DETAILED DESCRIPTION

Figure 1C:
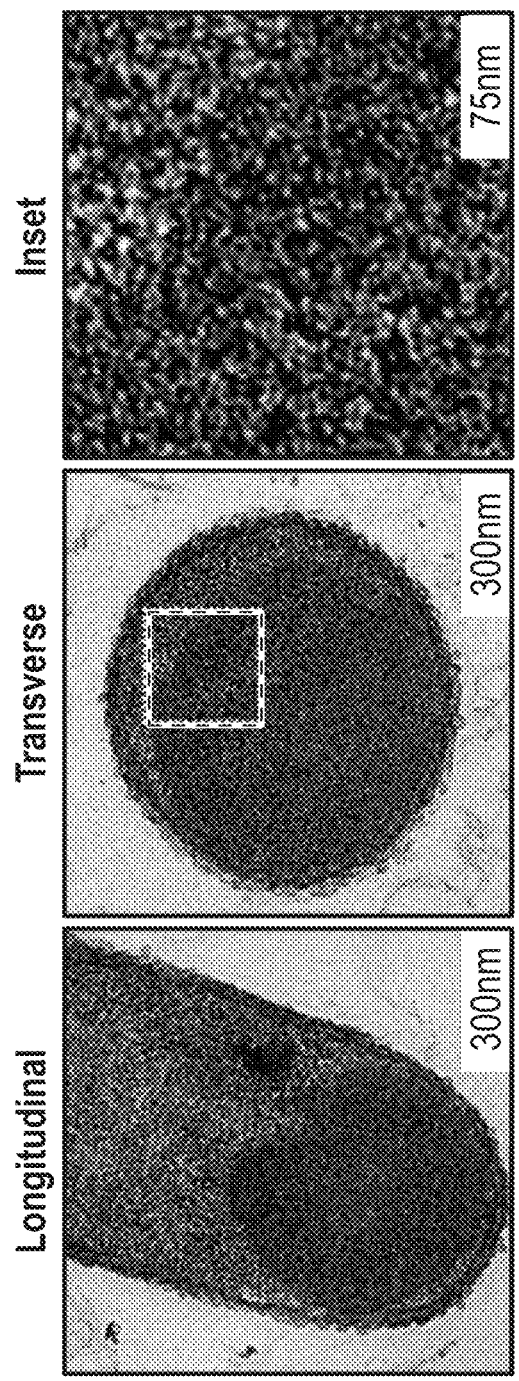

Self-assembling proteins are described herein that are useful as building blocks to construct nanoscaffolds that can recruit cargo molecules. Methods of visualizing scaffold-cargo formation dynamics in vivo are also described. For example, the protein scaffolds can have a tag or adaptor domain that can bind a reciprocal tag or adaptor on the targeted cargo molecules. Such tags/adaptors facilitate assembly of the cargo protein decorated scaffolds. The assembly of cargo protein onto the nanoscaffold can be visualized to permit tuning of scaffold protein and cargo expression levels.

As described herein, real-time observation reveals a nucleation-limited step where multiple scaffolds initially form within a cell and over time, nucleated scaffolds reorganize into a single intracellular assembly. Such reorganization can be due to inter-scaffold competition for protein subunits. Design considerations are described herein for using self-assembling proteins as building blocks to construct nanoscaffolds, while visualizing scaffold-cargo dynamics in vivo.

Nanoscaffold Proteins Bacterial microcompartment shell proteins such as those with a pfam0936-domain can be used as the protein-based scaffolds for constructing the nanometer scale scaffolds in vivo (see FIG. 1A). Proteins with this pfam0936-domain spontaneously oligomerize to form a "tile" of about 7 nm in diameter. As illustrated herein, conserved perimeter residues can laterally interact with other pfam0936-domain tiles in multiplicative protein-protein interactions, giving rise to higher-order nanoarchitectures inside cells. These higher order nanoarchitectures can recruit particular molecular cargo for building a diverse set of intracellular scaffolds.

However, several obstacles and questions remain in realizing the full potential for generating higher order nanoarchitectures formed by pfam00936 protein expression.

A library of pfam00936 domain-containing proteins was created by the inventors to generate a toolbox of components suitable for use as "Scaffolds Formed by BMC-Shell proteins" (referred to as ScaF proteins or ScaFS). The selected ScaFS had differences in primary structure that modified their surface electrostatics, lateral interface residues, and C-terminal extensions. Some of the Scaf proteins relate to or were obtained from Synechococcus elongatus PCC 7942 (CcmO), sequence shown below as SEQ ID NO:20 (NCBI accession no. P46205.2).

```
  1  MSASLPAYSQ PRNAGALGVI CTRSFPAVVG TADMMLKSAD

41  VTLIGYEKTG SGFCTAIIRG GYADIKLALE AGVATARQFE

81  QYVSSTILPR PQGNLEAVLP ISRRLSQEAM ATRSHQNVGA

121  IGLIETNGFP ALVGAADAML KSANVKLICY EKTGSGLCTA

161  IVQGTVSNVT VAVEAGMYAA FRIGQLNAIM VIPRPLDDLM
```

```
201  DSLPEPQSDS EAAQPLQLPL RVREKQPLLE LPELERQPIA

241  IEAPRLLAEE RQSALELAQE TPLAEPLELP NPRDDQ
```

The first 100 or so amino acids of the Synechococcus elongatus PCC 7942 (CcmO) sequence are sometimes referred to as the BMC 1 domain, with the BMC 2 domain from about amino acid position 102 to amino acid position 204. For example, a Synechococcus BMC 2 domain can have the following sequence (SEQ ID NO:21).

```
  1  MLKSANVKLI CYEKTGSGLC TAIVQGTVSN VTVAVEAGMY

41  AAERIGQLNA IMVIPRPLDD LMDSLPEPQS DSEAAQPLQL

81  PLRVREKQPL LELPELERQP IAIEAPRLLA EERQSALELA

121  QETPLAEPLE LPNPRDDQ
```

A Synechococcus carbon dioxide-concentrating mechanism protein CcmK has the following sequence (SEQ ID NO:22; NCBI accession no. WP_011242445.1.

```
  1  MSASLPAYSQ PRNAGALGVI CTRSFPAVVG TADMMLKSAD

41  VTLIGYEKTG SGFCTAIIRG GYADIKLALE AGVATARQFE

81  QYVSSTILPR PQGNLEAVLP ISRRLSQEAM ATRSHQNVGA

121  IGLIETNGFP ALVGAADAML KSANVKLICY EKTGSGLCTA

161  IVQGTVSNVT VAVEAGMYAA ERIGQLNAIM VIPRPLDDLM

201  DSLPEPQSDS EAAQPLQLPL RVREKQPLLE LPELERQPIA

241  IEAPRLLAEE RQSALELAQE TPLAEPLELP NPRDDQ
```

Other ScaF related sequences can be obtained from Synechococcus elongatus PCC 7942 CcmK2 protein, sequence shown below as SEQ ID NO:23 (NCBI accession no. Q03511.1).

```
  1  MPIAVGMIET LGFPAVVEAA DAMVKAARVT LVGYEKIGSG

41  RVTVIVRGDV SEVQASVSAG LDSAKRVAGG EVLSHHIIAR

81  PPENLEYVLP IRYTEAVEQF PM
```

Various primary sequences of selected pfam0936-domain proteins were compared. The sequences included CcmO sequences from Synechococcus elongatus PCC 7942, which was split into two pfam0936 domains (CcmO_1, SEQ ID NO:24) and domain 2 (CcmO_2, SEQ ID NO:25). Other sequences used in the comparison included Halothece sp. PCC 7418 CcmK1 (SEQ ID NO:26), Halothece sp. PCC 7418 CcmK2 (SEQ ID NO:27). Mycobacterium smegmatis (RmmH; SEQ ID NO:28). Citrobacter freundii (PduA; SEQ ID NO:29), and Haliangium ochraceum BMC-H 5815 (HO-BMC; SEQ ID NO:30). The sequence comparisons are shown below.

```
                    1         10        20        30
CcmO_2   (NO: 25)                                   MLKSAN
CcmO_1   (NO: 24)   MSASLPAYSQPRNAGALGVICTRSFPAVVGTADMMLKSAD
CcmK2    (NO: 27)                    MPIAVGMIETLGFPAVVEAADAMVKAAR
CcmK1    (NO: 26)                    MAVAVGMIETLGFPAVVEAADAMVKAAR
RmmH     (NO: 28)                    MSSNAIGLIETKGYVAALAAADAMVKAAN
PduA     (NO: 29)                    MQQEALGMVETKGLTAAIEAADAMVKSAN
Ho-BMC   (NO: 30)                    MADALGMIEVRGFVGMVEAADAMVKAAK
                                                *****↑

40        50        60        70
CcmO_2              VKLICYEKTGSGLCTAIVQGTVSNVTVAVEAGMYAAER
CcmO_1              VTLIGYEKTGSGFCTAIIRGGYADIKLALEAGVATARQ
CcmK2               VTLVGYEKIGTGRVTVIVRGDVSEVQASVSAGVDSANRVN
CcmK1               VTLVGYEKIGTGRVTVIVRGDVSEVQASVSAGTESVKRVN
RmmH                VTITDRQQVGDGLVAVIVTGEVGAVKAATEAGAETASQ
PduA                VMLVGYEKIGSGLVTVIVRGDVGAVKAATDAGAAAARN
Ho-BMC              VELIGYEKTGGGYVTAVVRGDVAAVKAATEAGQRAAER
                    * *    * *        *         **

80        90        100
CcmO_Domain2        IGQLNAIMVIPRPLDDLMDSLPEPQSDSEAAQPLQLPLRV
CcmO_Domain1        FEQYVSSTILPRPQGNLEAVLPISRRLSQEAMA        T
CcmK2               GGEVLSTHIIARPHENLEYVLPIRYTEAVEQFR
CcmK1               GGQVLSTHIIARPHENLEYVLPIRYTEEVEQFR        E
RmmH                VGELVSVHVIPRPHSELGAHFSVSSK
PduA                VGEVKAVHVIPRPHTDVEKILPKGIRLVKDPA
Ho-BMC              VGEVVAVHVIPRPHVNDAALPLGRTPGMDKSA
                         * **

110       120       130
CcmO_Domain2        REKQPLLELPELERQPIAIEAPRLLAEERQSALELAQETP
CcmO_Domain1        RSHQN              VGAIGLIETNGFPALVGAADA
CcmK1               GV                 GTPRNITRQ
CcmO_Domain2        LAEPLELPNPRDDQ
```

Such comparisons identify regions, domains, and amino acids with sequence similarities and sequence differences. Regions of homology or sequence identity are identified by asterisks below the sequences.

Previous work had indicated that these sequence differences can influence self-assembly properties, and it has previously been difficult to predict how modifying primary sequence (e.g. single amino acid substitutions or domain extensions) would translate into the type(s) of higher-order architectures that form (Young et al., 2017).

Visualization of the intracellular ScaFS assembly by transmission electron microscopy (TEM) of cellular thin sections identified seven candidate ScaFs. These seven ScaFs formed discrete structures that could be visualized by TEM (including tubes, sheets, and "rosettes"; FIG. 1E). Two ScaFS from Halothecee sp. PCC 7418, did not form discernable nanoarchitectures in the cytosol of E. coli, although SDS-PAGE analysis indicated they were correctly expressed.

An Haliangium ochraceum (HO) BMC-H 5815 (Lassila et al., 2014; Young et al., 2017) ScaFS was selected to evaluate the effects of appending an additional adaptor domain useful for mediating protein-protein interactions. This 5815 ScaFS domain has the following sequence (SEQ ID NO:1).

```
  1   MADALGMIEV RGFVGMVEAA DAMVKAAKVE LIGYEKTGGG
 41   YVTAVVRGDV AAVKAATEAG QRAAERVGEV VAVHVIPRPH
 81   VNVDAALPLG RTPGMDKSA
```

Additional ScaFs were made by modification of the wild type 5815 Haliangium ochraceum ScaF. For example, a modified 5815 ScaF with an alanine substitution at position 28 to replace the lysine (K28A). The sequence of this K28A 5815 ScaF is shown below as SEQ ID NO:2 (with the substituted alanine highlighted in bold and with underlining).

```
  1   MADALGMIEV RGFVGMVEAA DAMVKAAAVE LIGYEKTGGG
 41   YVTAVVRGDV AAVKAATEAG QRAAERVGEV VAVHVIPRPH
 81   VNVDAALPLG RTPGMDKSA
```

In another example, a modified 5815 ScaF has a proline substitution at position 28 to replace the lysine (K28P). The sequence of this K28P 5815 ScaF is shown below as SEQ ID NO:3 (with the substituted proline highlighted in bold and with underlining).

```
  1   MADALGMIEV RGFVGMVEAA DAMVKAAPVE LIGYEKTGGG
 41   YVTAVVRGDV AAVKAATEAG QRAAERVGEV VAVEVIPRPH
 81   VNVDAALPLG RTPGMDKSA
```

In another example, a modified 5815 ScaF has an alanine substitution at position 78 to replace the arginine (R78A). The sequence of this R78A 5815 ScaF is shown below as SEQ ID NO:4 (with the substituted alanine highlighted in bold and with underlining).

```
  1   MADALGMIEV RGFVGMVEAA DAMVKAAKVE LIGYEKTGGG
 41   YVTAVVRGDV AAVKAATEAG QRAAERVGEV VAVHVIPAPH
 81   VNVDAALPLG RTPGMDKSA
```

The scaffold (ScaF) proteins can have sequence variability. For example, the scaffold (ScaF) protein sequences can have 1%, or 2%, or 3%, or 4%, or 5% sequence variability.

In other words, the scaffold (ScaF) proteins can have at least 95% sequence identity, or 96% sequence identity, or 97% sequence identity, or 98% sequence identity, or 99% sequence identity, or 99.5% sequence identity to the scaffold (ScaF) protein sequences described herein.

Adaptor Tags for Binding Between Scaffold Proteins and Cargo Proteins

The adaptor tags employed were specifically designed to provide non-covalent binding of the scaffold proteins to cargo proteins. This allows the scaffold (ScaF) complex to initiate formation without interference from the cargo proteins. In addition, unlike covalently linked scaffold-cargo protein constructs, an independent scaffold protein construct with established assembly properties can be employed with a variety of cargo proteins.

Heterodimeric, coiled-coil protein domains termed "Synthetic Zippers (SZ; Thompson et al., 2012) were selected to be appended to the scaffold proteins as tags or adaptors to provide sites for cargo protein binding.

Pairs of such Synthetic Zippers are designed bind together. For example, SYNZIP1 (SZ1) and SYNZIP2 (SZ2) bind together, and in another example SYNZIP5 (SZ5) and SYNZIP6 (SZ6) bind together. Hence, one member of a selected pair of Synthetic Zippers can be linked to a scaffold protein (ScaF) and the other member of the Synthetic Zipper pair can be linked to a selected cargo protein. The scaffold protein-synthetic zipper (Scaf-SZ) can then be expressed in a cell with a selected cargo protein-synthetic zipper (cargo-SZ) to generate an intracellular scaffold that binds the selected cargo protein.

The Synthetic Zippers can be fused in frame to the N-terminus or C-terminus of the ScaF. However, in the experiments shown herein, the Synthetic Zippers were fused to the C-terminus of the ScaFs because pfam00936-domain containing proteins like the ScaFs described herein exhibit considerable diversity in the size and composition in their extensions at the C-terminus. In some cases, therefore, the Synthetic Zippers are fused in frame to the C-terminus of the ScaF.

Any synthetic zipper pair can be employed where one member of the pair is linked to the scaffold (ScaF) protein while the other member of the pair is linked to the cargo protein. A number of synthetic zipper proteins are described by Thompson et al. (ACS Synth. Biol. 1: 118-129 (2012)), which is incorporated herein by reference in its entirety.

One example of a synthetic zipper that can be used is Synthetic Zipper 5 (SZ5), which has the following sequence (SEQ ID NO:5).

```
 1    NTVKELKNY IQELEERNA ELKNLKEHLK FAKAELEFE

41    LAAHKFE
```

An example of a synthetic zipper that binds SZ5 is Synthetic Zipper 6 (SZ6), which has the following sequence (SEQ ID NO:6).

```
 1    MQKVAQLKNR VAYKLKENAK LENIVARLEN DNANLEKDIA

41    NLEKDIANLE RDVAR
```

These Synthetic Zipper adapters provide significantly expanded interactome of binding affinities and orientations with demonstrated functionality both in vivo and in vitro.

The synthetic zipper proteins can have sequence variability. For example, the synthetic zipper protein sequences can have 1%, or 2%, or 3%, or 4%, or 5% sequence variability.

In other words, the synthetic zipper proteins can have at least 95% sequence identity, or 96% sequence identity, or 97% sequence identity, or 98% sequence identity, or 99% sequence identity, or 99.5% sequence identity to the synthetic zipper protein sequences described herein.

Linkers

Linkers can be used to link the Synthetic Zipper adaptors to the Scaffold (ScaF) proteins and to link the Synthetic Zipper adaptors to the cargo proteins. The linkers between the scaffold (ScaF) and Synthetic Zipper proteins were designed to be flexible, with a high content of glycine and serine residues, because experiments demonstrated that rigid linkers inhibited scaffold formation. For example, only amorphous electron dense regions with characteristics similar to protein inclusion bodies were observed following expression scaffold proteins linked Synthetic Zippers via proline-rich rigid linkers.

Conversely, Synthetic Zipper linked to the scaffold (ScaF) protein via a flexible glycine-rich linkers formed curved, sheet-like structures within the cytosol that maintained a higher-order arrangement similar to scaffold proteins without the synthetic zipper tag. The sheet-like structures formed by ScaF-flexible linker-Synthetic Zipper constructs tended to pack in a less dense arrangement, for example as a webwork of curls, rather than as a dense unorganized mass.

Hence, the linkers employed are flexible because they contain a high percentage of glycine and/or serine residues. The linkers can include, for example, at least 60%, at least 70%, at least 80%, at least 90%, or at least 95% glycine residues, serine residues, or a combination of glycine and serine residues.

The linkers can have about 3 to 20 amino acids. For example, the linkers can have three or more amino acids, or four or more amino acids, or five or more amino acids, or six or more amino acids, or seven or more amino acids, or eight or more amino acids, or nine or more amino acids, or ten or more amino acids, or eleven or more amino acids, or twelve or more amino acids, or thirteen or more amino acids, or fourteen or more amino acids, or fifteen or more amino acids. The amino acids included in the flexible linkers include glycine and serine. In general, the flexible linkers do not include proline.

For example, a GGGGS linker (SEQ ID NO:7) can be used a flexible linker. Such a linker can have additional amino acids, such as one or more additional amino acids, or two or more additional amino acids, or three or more additional amino acids, or four or more additional amino acids, or five or more additional amino acids. The additional amino acids are not proline amino acids.

Cargo Proteins

The scaffold (ScaF) protein can assemble into intracellular scaffold that can recruit a variety of cargo proteins. In some cases, the cargo proteins are: enzymes for increasing bioproduction of commodities (e.g. perfumes or dyes); enzymes for production of food materials (starches, polysaccharides, proteins, oils), or enzymes for production of fuels (e.g. butanol or ethanol); fluorescent proteins for imaging structure and dynamics; and enzymes as contrast enhancing agents for electron or x-ray based imaging methodology.

Markers or Tags

The Scaffold and/or Synthetic Zipper proteins can include a marker or tag that facilitates identification or collection of the protein. Such markers or tags can, for example, provide a detectable signal or be useful for isolation of Scaffold proteins, Synthetic Zipper proteins, or a complex that includes the Scaffold and/or Synthetic Zipper proteins. For example, the Scaffold and/or Synthetic Zipper proteins can include an epitope tag so that the proteins can be precipitated from a mixture or so that the proteins can be quantified or tracked during an experiment.

One example of such a marker or tag is a hemagglutinin (HA) tag, which can have the following sequence: YPYDVPDYA (SEQ ID NO:8). Another example is a StrepII tag, which can have the following sequence: WSHPQFEK, a histidine tag (a peptide with a series of histidines, or an epitope for another particular antibody.

Fluorescent cargo proteins can also be markers or tags. For example, such fluorescent proteins can be used for monitoring assembly of the scaffold and the cargo proteins. Examples of fluorescent proteins that can be used include mNeonGreen, mScarlet-I, mMaple3, and the like.

Expression Systems

Nucleic acid segments encoding a scaffold or cargo protein can be inserted into or employed with any suitable expression system. Recombinant expression of nucleic acids is usefully accomplished using a vector, such as a plasmid. The vector can include a promoter operably linked to nucleic acid segment encoding a scaffold or cargo protein. The vector can also include other elements required for transcription and translation.

As used herein, vector refers to any carrier containing exogenous DNA. Thus, vectors are agents that transport the exogenous nucleic acid into a cell without degradation and include a promoter yielding expression of a protein encoded by the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing scaffold or cargo proteins. The vectors can be used, for example, in a variety of in vivo situations.

The expression cassette, expression vector, and sequences in the cassette or vector can be heterologous. As used herein, the term "heterologous" when used in reference to an expression cassette, expression vector, regulatory sequence, promoter, or nucleic acid refers to an expression cassette, expression vector, regulatory sequence, or nucleic acid that has been manipulated in some way. For example, a heterologous promoter can be a promoter that is not naturally linked to a nucleic acid of interest, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA forms. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

A variety of prokaryotic expression vectors can be used. For example, prokaryotic expression vectors include pET vectors, pBbB6k vectors, pBbA2a vectors, pUC vectors, pTrcHis vectors, pZA31-luc, pZE12-luc, pZB, pTrc99A, pBAD33, pPro24, pPro29b, and the like. See, e.g., Lee et al., J Biol Eng 5:12 (2011).

Viral vectors that can be employed include those relating to lentivirus, adenovirus, adeno-associated virus, herpes virus, vaccinia virus, polio virus. AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232. Washington. (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a scaffold or cargo protein.

A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

In some cases, the promoter is used without an enhancer.

Expression vectors used in eukaryotic host cells (yeast, fungi, insect, plant, animal, human or nucleated cells) can also contain sequences for the termination of transcription, which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The expression of a scaffold or cargo protein from an expression cassette or expression vector can be controlled by any promoter capable of expression in prokaryotic cells or eukaryotic cells. Examples of prokaryotic promoters that can be used include, but are not limited to: SP6, T7, T5, tac, bla, trp, gal, lac, Tet, Trc, ProS, ProE, Lac, BAD, AraC, or maltose promoters. However, in some cases, the promoter is not a constitutive promoter. For example, in some cases, the promoter is not a T7 promoter.

Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the IPTG inducible (lac repressor) promoter, tet promoter, arabinose-inducible promoter, lactose-inducible promoter, propionate-regulated promoter, the hsp70 promoter, and a synthetic promoter regulated by cis-regulatory element (CRE).

The expression cassette or vector can include nucleic acid sequence encoding a marker product. This marker product is used to determine if the gene has been delivered to the cell and once delivered is being expressed. Marker genes can include and antibiotic, the *E. coli* lacZ gene which encodes β-galactosidase, or a fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs ampicillin, neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468. (1990); and Wolff, J. A. Nature, 352, 815-818, (1991).

For example, the scaffold or cargo nucleic acid molecule, expression cassette and/or vector can be introduced to a cell by any method including, but not limited to, calcium-mediated transformation, electroporation, microinjection, lipofection, particle bombardment and the like. The cells can be expanded in culture to form a population of transformed cells.

Methods of Preparing the Cells for Scaffolds

Figure 5A:
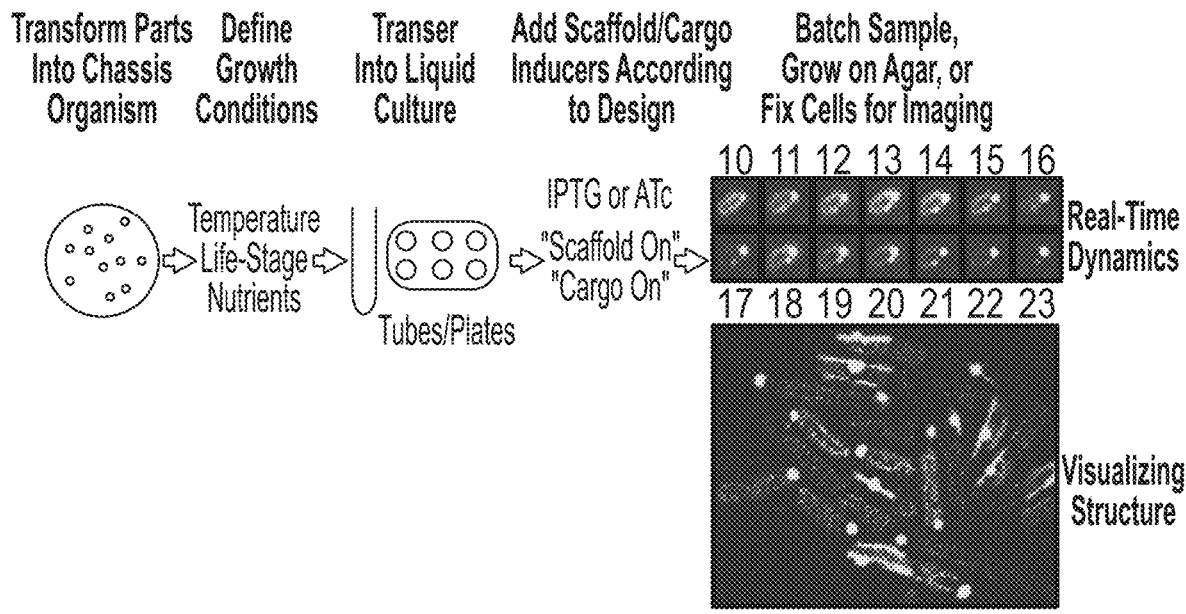
FIG. 5A-5B schematically illustrates an exemplary methodology for imaging nanoscaffold assembly in living cells.
Figure 5B:
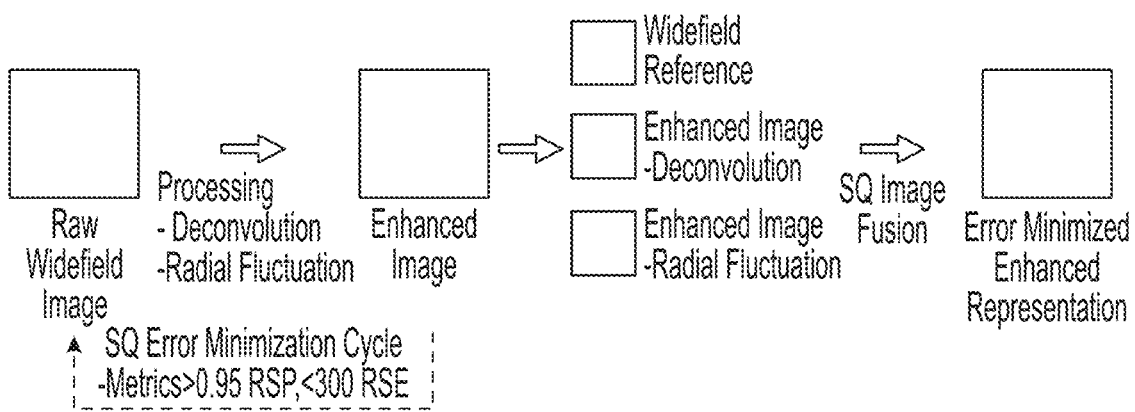

As illustrated in FIG. 5A, one of the first steps is to transform host cells to include one or more expression cassettes ("chassis") that encode one or more scaffold protein-Synthetic Zipper and one or more cargo protein-Synthetic Zipper.

In some cases, at least one scaffold protein-Synthetic Zipper and at least one cargo protein-Synthetic Zipper can be expressed from one or more expression cassettes in the same expression vector. This can ensure that expression cassettes for the scaffold and cargo proteins are all together within the host cell.

However, it can be useful to separately control the expression of scaffold protein and cargo proteins. Hence, in some cases the expression cassettes for at least one scaffold protein construct are separate from the expression cassettes for at least one cargo protein construct. In such cases, it may be useful to prepare separate expression vectors for the scaffold protein constructs and the cargo protein constructs.

In another step, illustrated for example in FIG. 5A, the host cells with the expression cassettes/vectors can be cultured and the scaffold and cargo proteins can be expressed.

Expression of the scaffold protein and the cargo protein constructs is preferably controlled. For example, overexpression of these constructs can have negative effects on the host cells such as slow growth and poor scaffold assembly. Hence, inducible expression can be used to turn on and off expression for selected periods of time. In some cases, expression of the scaffold proteins can also be initiated before expression of the cargo proteins to allow the scaffold to initiate assembly before the cargo protein decorates it.

Hence, selected agents ("inducers" or "inducing agents") that induce expression of the scaffold protein and/or the cargo protein can be added to the culture medium. Different inducers can be used for inducing expression of the scaffold protein and the cargo protein so that the host cells can synthesize these proteins at different times. See FIG. 5A.

Examples of inducing agents that can be used include isopropyl β-D-1-thiogalactopyranoside (IPTG), 1-arabinose, anhydrotetracycline (aTc), lactose, propionate, tetracycline, and temperature shifts (from 37 to 42° C.).

For example, in some cases the host cells can be grown with an inducer of scaffold protein expression for a time sufficient for synthesis of enough scaffold protein to initiate scaffold assembly. An inducer of cargo protein synthesis can then be added so the host cells begin synthesis of the cargo proteins.

Use of tunable inducible promoters of low-to-moderate activity led to tighter control over scaffold formation, more predictable recruitment of intended cargo proteins, and reduced cellular burden. As used herein a "tunable" promoter can be activated by an inducer in a concentration-dependent manner. For example, the concentration of small molecules (isopropyl β-D-1-thiogalactopyranoside, arabinose, lactose, tetracycline, etc.) in the culture medium can be directly proportional to the expression levels induced by the tunable promoter.

A range of inductions were investigated by titrating in differing concentrations of isopropyl β-D-1-thiogalactopyranoside. The proper range expression provided control in cellular morphology, cellular size, and number of structures formed in cells. This is in contract to prior publications in the field because they have historically relied on high-expression promoters (e.g., T7-based). Use of such high-expression promoters is ill-suited for scaffolding applications because high expression of BMC shell proteins harms physiology, deforms cell morphology, inhibits division, and promotes untimely cell death. Furthermore, the leaky expression and non-tunability typical of high-expression promoters makes complicates analysis of initial scaffold assembly.

Examples of tunable or inducible promoters include tetracycline-regulated gene expression systems (Ptet and tetR)

(Lee et al., J Bacteriol. 187(8):2793-800 (2005)), propionate-regulated gene expression systems (PprpB and prpR) (Lee et al., Appl Environ Microbiol. 71(11):6856-62 (2005); Lee et al., Protein Expr Purif. 61(2):197-203 (2008)), the alkane-inducible promoter (PalkB), the phosphate-regulated promoters (Pugp), and the arabinose-inducible promoter system (PBAD and araC) (Guzman et al., J Bacteriol. 177(14):4121-30 (1995)).

Examples of promoter sequences are available in the NCBI database. For example, arabinose-inducible promoters can have sequences such as those with accession numbers OK148698.1 (GI:2108243001); or J01641.1 (GI:145314).

Scaffold formation and scaffold-cargo protein co-assembly can be monitored within live or fixed cells. See FIG. 5A. In some cases, the cells can be maintained alive while monitoring assembly of the scaffold and the association of the cargo protein with the scaffold, for example, by observing movement a fluorescent marker on the scaffold protein or the cargo protein. In other cases, the cells can be fixed, and the cellular structures observed within the fixed cells.

Detecting and Monitoring Scaffold Formation

Intracellular structures can be visualized by a light microscope or an electron microscope. For example, in some cases transmission electron microscopy (TEM), or scanning electron microscopy can be used. Whole cells or sections of cells can be visualized. However, in some cases it is useful to express a fluorescent protein as a cargo protein to visualize the process of cargo protein—scaffold formation. For example, expression of a fluorescent cargo protein with another selected cargo protein allows the association of both cargo proteins with the scaffold.

Methods for observing and monitoring scaffold formation and cargo protein association with the scaffold can include observing raw widefield images, processing of the images using deconvolution and/or radial fluctuation, observing enhanced images, consideration of widefield references, further deconvolution of enhanced images, further enhancement of images by radial fluctuation, fusion of images (e.g., SQ image fusion), or a combination thereof to produce an error minimized enhanced representation of the monitoring scaffold formation and cargo protein association.

Imaging real-time dynamics of scaffold assembly in cells required determining suitable reporter labels, engineering exact temporal control of expression, and devising extended microscopic imaging conditions for living cells. Real-time imaging with light microscopy of live-cell populations allowed the inventors to investigate the first stages of scaffold assembly and subsequent dynamics. Analysis demonstrated a nucleation-driven mechanism to scaffold formation. The constructs and methods described herein demonstrate how effectively Synthetic Zipper-functionalized fluorescent proteins in conjunction with Synthetic Zipper-functionalized Scaffold proteins can intracellularly assemble. Not only are the constructs described herein optimized be the methods also optimized the dynamics of assembly.

The following Examples illustrate some of the experimental work involved in development of the invention. Additional information may be available in Appendices A and B, as well as Young et al. Nano Letter 20: 208-217 (2020), which is incorporated by reference herein in its entirety.

Example 1: Materials and Methods

This Example describes some of the materials and methods used in developing the invention.

Cloning of Assembly and Cargo Module Constructs

Genes were synthesized by Integrated DNA Technologies. Isothermal assembly was used to clone sequences into their respective destination plasmids (pET11b, pBbB6k, pBbA2a). *E. coli* DH5a strains were used for plasmid construction and propagation (see Tables I and 2 for plasmid types, inserts, and resistance markers).

TABLE 1

Plasmids and gene inserts

| Plasmid | Insert |
| --- | --- |
| pET | HO BMC-H 5815 |
| pET | K25A_HO BMC-H 5815 |
| pET | Y41A_HO BMC-H 5815 |
| pET | K28A_HO BMC-H 5815 |
| pET | K28P_HO BMC-H 5815 |
| pET | R78A_HO BMC-H 5815 |
| pET | CcmK2 (7418) |
| pET | CcmK1 (7418) |
| pET | PduA* |
| pET | RmmH |
| pET | HO BMC-H 5815ppgSZ5 |
| pET | K25A_HO BMC-H 5815ppgSZ5 |
| pET | Y41A_HO BMC-H 5815ppgSZ5 |
| pET | K28A_HO BMC-H 5815ppgSZ5 |
| pET | K28P_HO BMC-H 5815ppgSZ5 |
| pET | HO BMC-H 5815ggsSZ19 |
| pET | K25A_HO BMC-H 5815ggsSZ19 |
| pET | K28P_HO BMC-H 5815ggsSZ19 |
| pET | R78A_HO BMC-H 5815ggsSZ19 |
| pET | HO BMC-H 5815ggsSZ5 |
| pET | K25A_HO BMC-H 5815ggsSZ5 |
| pET | K28A_HO BMC-H 5815ggsSZ5 |
| pET | K28P_HO BMC-H 5815ggsSZ5 |
| pET | R78A_HO BMC-H 5815ggsSZ5 |
| pBbB6k | HO BMC-H 5815 |
| pBbB6k | K28A_HO BMC-H 5815 |
| pBbB6k | K28P_HO BMC-H 5815 |
| pBbB6k | R78A_HO BMG-H 5815 |
| pBbB6k | HO BMC-H 5815ggsSZ5 |
| pBbB6k | K25A_HO BMC-H 5815ggsSZ5 |
| pBbB6k | K28A_HO BMC-H 5815ggsSZ5 |
| pBbB6k | K28P_HO BMC-H 5815ggsSZ5 |
| pBbB6k | R78A_HO BMC-H 5815ggsSZ5 |
| pBbB6k | STREP-mNeonGreen |
| pBbB6k | STREP-mMaple3 |
| pBbB6k | SZ6-ggs-mNeonGreen |
| pBbB6k | SZ18-ggs-mNeonGreen |
| pBbA2a | STREP-mMaple3 |
| pBbA2a | STREP-mNeonGreen |
| pBbA2a | SZ6-ggs-mNeonGreen |
| pBbA2a | STREP-mScarlet-I |
| pBbA2a | SZ6-ggs-mScarlet-I |
| pBbA2a | SZ16-ggs-mScarlet-I |
| pBbE8c | STREP-mScarlet-I |
| pBbE8c | SZ6-ggs-mMaple3 |
| pBbE8c | SZ6-ggs-APEX2 |
| pBbE8c | SZ21-ggs-mScarlet-I |
| pBbS8c | SZ6-ggs-mNeonGreen |
| pBbS8c | SZ6-ggs-mScarlet-I |
| pBbA2a | SZG-ggs-mMaple3 |
| pBbA2a | SZG-ppg-mMaple3 |

FIG. 1G is a schematic diagram of expression cassettes for a Synthetic Zipper-Scaffold (ScaF) protein construct and for a Synthetic Zipper Fluorescent cargo protein construct.

TABLE 2

Plasmid Resistance Markers

| Plasmid | Gene | Resistance |
| --- | --- | --- |
| 1 | pET-11b | HO BMC-H 5815 AMP |
| 2 | pET-11b | K28A_HO BMC-H 5815AMP |

TABLE 2-continued

Plasmid Resistance Markers

| Plasmid | Gene | Resistance |
|---|---|---|
| 3 | pET-11b | K28P_HO BMC-H 5815AMP |
| 4 | pET-11b | R78A_HO BMC-H 5815AMP |
| 5 | pET-11b | CcmK2 (7418) AMP |
| 6 | pET-11b | CcmK1 (7418) AMP |
| 7 | pET-11b | PduA AMP |
| 8 | pET-11b | RmmH AMP |
| 9 | pET-11b | HO BMC-H 5815ppgSZ5-HA AMP |
| 10 | pET-11b | HO BMC-H 5815ggsSZ5-HA AMP |
| 11 | pET-11b | K28A_HO BMC-H 5815ggsSZ5-HA AMP |
| 12 | pET-11b | K28P_HO BMC-H 5815ggsSZ5-HA AMP |
| 13 | pET-11b | R78A_HO BMC-H 5815ggsSZ5-HA AMP |
| 14 | pET-11b | HO BMC-H 5815ggsSZ19-HA AMP |
| 15 | pBbB6k | HO BMC-H 5815ggsSZ5-HA KAN |
| 16 | pBbB6k | K28A_HO BMC-H 5815ggsSZ5-HA KAN |
| 17 | pBbB6k | STREP-mNeonGreen KAN |
| 18 | pBbB6k | SZ6-ggs-mNeonGreen KAN |
| 19 | pBbA2a | STREP-mNeonGreen AMP |
| 20 | pBbA2a | SZ6-ggs-mNeonGreen AMP |
| 21 | pBbA2a | STREP-mScarlet-I AMP |
| 22 | pBbA2a | SZ6-ggs-mScarlet-I AMP |

Expression of Assembly and Cargo Modules

E. coli BL21 ArcticExpress (DE3) competent cells (Agilent) were used for cellular expression studies. Competent cells were transformed with constructs containing the gene(s) of interest and plated on LB agar plates with the appropriate antibiotic(s) to provide selection. Individual colonies were picked into 5 mL LB cultures with the appropriate antibiotics(s) and incubated at 30° C., with a rotational stirring of 250 RPM. These overnight cultures were inoculated 1:100 into fresh liquid cultures with conditions dependent upon the experimental plan. For TEM analysis, cells were inoculated in 50 mL LB, grown until ~$OD_{600}$ 0.8, induced with 100 µM IPTG, and incubated for an additional 6 hours, before 2 mL of the parent culture was fixed overnight at 4° C. Cells used to purify protein were cultured in a similar manner, the whole culture was pelleted, and cell pellets were stored at −20° C. for subsequent protein isolation. Cultures analyzed via light microscopy were inoculated into 1 mL LB or SOB media in culture tubes and incubated the indicated amount of time before imaging. Appropriate inducer(s) (IPTG or aTc) were added as indicated for each experimental design.

Purification of Assembly and Cargo Proteins

Pellets were solubilized in 30 mL resuspension buffer (50 mM Tris pH 7.8, 100 mM NaCl. 10 mM $MgCl_2$) on ice, lysed in a cell disruptor at 20 k psi, and centrifuged at 20 k g to separate soluble and insoluble fractions. For assembly module isolation, pellets were washed about 3 times with resuspension buffer+1% Triton X-100, followed by washes with 500 mM NaCl resuspension buffer. ScaF protein was stored at 4° C. until further analysis. Cargo modules were purified from the soluble cellular lysis fraction using Streptactin resin (IBA) according to the manufacture's protocol.

Magnetic Bead Precipitation

Purified cargo and ScaF modules (about 20 µg each) were added together and allowed to mix gently for 2 hours on a rotator at room temperature. Washed Anti-HA Magnetic Beads (Pierce) were added to the solution and incubated for 30 minutes in order to allow binding to the HA tags appended to the C-terminus of ScaF constructs. Beads were then magnetically collected, washed three times, and then eluted with 0.5 M NaOH and analyzed via SDS-PAGE gel electrophoresis.

Transmission Electron Microscopy Thin Section Analysis

Expression of shell proteins was driven from T7 promoters as described above, then 2 mL cell aliquots were fixed in 2.5% glutaraldehyde/paraformaldehyde in sodium cacodylate buffer overnight at 4° C. Cells were pelleted by centrifugation at 4 k rpm for 2 minutes and washed with sodium cacodylate buffer three times. Samples then were processed with a microwave assisted protocol beginning with 1% osmium tetroxide. Cells were washed with HPLC-grade water until clear, and stained with 2% uranyl acetate, followed by another wash cycle. Samples were dehydrated with a gradient acetone series, then infiltrated with Spurr resin and cured at 60° C. for ~3 days. Blocks were trimmed to highlight areas of cellular concentration and then ultrathin sectioned on an RMC MX ultra-microtome with a diamond knife (Diatome 45°). Sections (~50 nm) were collected on copper mesh grids and stained subsequently with 2% uranyl acetate, washed, and then incubated with Reynolds lead citrate for 5 minutes each. Imaging was performed on a JEM 100CX II transmission electron microscope (JEOL) with a Prius SC200-830 CCD camera (Gatan). Raw data files were processed with FIJI-ImageJ software.

Light Microscopy

Cells were imaged on either a Zeiss Observer D1 or Zeiss Elyra P1 microscope. Suspended cells (1-3 µL) were loaded onto an agarose pad and covered with a coverslip to minimize cell movement. These agarose pads were composed of M9 medium+1% agarose (Thermo Fisher). Samples imaged with Structured Illumination Microscopy were collected as Zstacks (5% power, 5 grid). Frames were collected in total internal reflectance mode (15% power, about 200 nm Zeiss software depth) as a Z-stack through each field every single minute. All raw data was processed with FIJI-ImageJ software.

Image Processing and Analysis

FIJI-ImageJ software was used in the processing and analysis of all raw data files (Schindelin. J. et al. 2012). Transmission electron microscopy thin section examples were all equally processed with a 'Enhance Local Contrast' plugin function. Deconvolution examples of widefield images used plugin 'Iterative Deconvolve 3D' utilizing an estimated measured point-spread function (PSF) of the Zeiss Observer D1. Total internal reflectance and structured illumination microscopy Z-stack frames were compiled using a 'Max Intensity Stack Projection.' In time lapse examples, frames were registered with 'Correct 3D Drift' plugin before stack formation. Values for foci development were tracked by measuring parameters within a circular region of interest in comparison to a reference area within a cell that lacked discernable features. Widefield microscopy images further processed by NanoJ-SRRF, and subsequent NanoJ-Squirrel error minimization, followed parameters specified in an experiment. Images were further processed with median, unsharp mask, or tophat filters as indicated.

Example 2: Designing ScaFs Nanoscaffolds

This Example describes experiments for identifying scaffold proteins that can be assembled into intracellular nanoscaffolds.

A library of pfam00936 domain-containing proteins was created to generate a toolbox of components suitable for use as "Scaffolds Formed by BMC-Shell proteins" (hereafter; ScaFS). Nine different ScaFS were individually expressed under a strong promoter (PT7) and their intracellular assembly was visualized by transmission electron microscopy (TEM) of cellular thin sections (FIG. 1B, 1F).

Various primary sequences of selected pfam0936-domain proteins were compared. The sequences included CcmO sequences from *Synechococcus elongatus* PCC 7942, which was split into two pfam0936 domains (CcmO, SEQ ID NO:24) and domain 2 (CcmO), SEQ ID NO:25). Other sequences used in the comparison included Halothece sp. PCC 7418 CcmK1 (SEQ ID NO:26), Halothece sp. PCC 7418 CcmK2 (SEQ ID NO:27) *Mycobacterium smegmatis* (RmmH; SEQ ID NO:28), *Citrobacter freundii* (PduA; SEQ ID NO:29), and *Haliangium ochraceum* BMC-H 5815 (HO-BMC; SEQ ID NO:30). A comparison sequence of these sequence is shown below.

```
  1   MADALGMIEV RGFVGMVEAA DAMVKAAKVE LIGYEKTGGG
 41   YVTAVVRGDV AAVKAATEAG QRAAERVGEV VAVEVIPRPH
 81   VNVDAALPLG RTPGMDKSA
```

Heterodimeric, coiled-coil protein domains from a toolbox, termed "Synthetic Zippers (SZ; Thompson et al., 2012) were selected to be appended to the 5815 ScaFS domain. Because pfam00936-domain containing proteins like the 5815 ScaFS domain naturally exhibit considerable diversity in the size and composition in extensions at the C-terminus,

```
                              1         10        20        30
CcmO_2        (NO: 25)                                        MLKSAN
CcmO_1        (NO: 24)   MSASLPAYSQPRNAGALGVICTRSFPAVVGTADMMLKSAD
CcmK2         (NO: 27)              MPIAVGMIETLGFPAVVEAADAMVKAAR
CcmK1         (NO: 26)              MAVAVGMIETLGFPAVVEAADAMVKAAR
RmmH          (NO: 28)              MSSNAIGLIETKGYVAALAAADAMVKAAN
PduA          (NO: 29)              MQQEALGMVETKGLTAAIEAADAMVKSAN
Ho-BMC        (NO: 30)              MADALGMIEVRGFVGMVEAADAMVKAAK
                                              *****↑

40        50        60        70
CcmO_2                   VKLICYEKTGSGLCTAIVQGTVSNVTVAVEAGMYAAER
CcmO_1                   VTLIGYEKTGSGFCTAIIRGGYADIKLALEAGVATARQ
CcmK2                    VTLVGYEKIGTGRVTVIVRGDVSEVQASVSAGVDSANRVN
CcmK1                    VTLVGYEKIGTGRVTVIVRGDVSEVQASVSAGTESVKRVN
RmmH                     VTITDRQQVGDGLVAVIVTGEVGABKAATEAGAETASQ
PduA                     VMLVGYEKIGSGLVTVIVRGDVGAVKAATDAGAAAARN
Ho-BMC                   VELIGYEKTGGGYVTAVVRGDVAAVKAATEAGQRAAER
                         * *      * *      *        **

80        90       100
CcmO_Domain2             IGQLNAIMVIPRPLDDLMDSLPEPQSDSEAAQPLQLPLRV
CcmO_Domain1             FEQYVSSTILPRPQGNLEAVLPISRRLSQEAMA         T
CcmK2                    GGEVLSTHIIARPHENLEYVLPIRYTEAVEQFR
CcmK1                    GGQVLSTHIIARPHENLEYVLPIRYTEEVEQFR         E
RmmH                     VGELVSVHVIPRPHSELGAHFSVSSK
PduA                     VGEVKAVHVIPRPHTDVEKILPKGIRLVKDPA
Ho-BMC                   VGEVVAVHVIPRPHVNVDAALPLGRTPGMDKSA
                              * **

110       120       130
CcmO_Domain2             REKQPLLELPELERQPIAIEAPRLLAEERQSALELAQETP
CcmO_Domain1             RSHQN              VGAIGLIETNGFPALVGAADA
CcmK1                    GV                 GTPRNITRQ
CcmO_Domain2             LAEPLELPNPRDDQ
```

The selected ScaFS had differences in primary structure that changed their C-terminal extensions, lateral interface residues and their surface electrostatics (FIG. 1E-1F). Previous work indicated that these sequence differences influence self-assembly properties, although was difficult to predict how modifying primary sequence (e.g. single amino acid substitutions or domain extensions) would translate into which type(s) of higher-order architectures that form (Young et al., 2017).

Seven candidate ScaFs formed discrete structures that could be visualized by TEM (including tubes, sheets, and "rosettes"; FIG. 1E) while two ScaFS from *Halothecee* sp. PCC 7418, did not form discernable nanoarchitectures in the cytosol of *E. coli*, even though SDS-PAGE analysis indicated they were correctly expressed.

An *Haliangium ochraceum* (HO) BMC-H 5815 (Lassila et al., 2014; Young et al., 2017) ScaFS was selected to evaluate the effects of appending an additional adaptor domain useful for mediating protein-protein interactions. This HO 5815 ScaFS domain has the following sequence (SEQ ID NO:1).

the Synthetic Zippers were fused to the C-terminus of the 5815 ScaFS with one or two different linker sequences. The linker sequences were designed to be either "rigid" (proline-rich; ppg) or "flexible" (composed of glycine and serine; ggs).

Figure 1D:
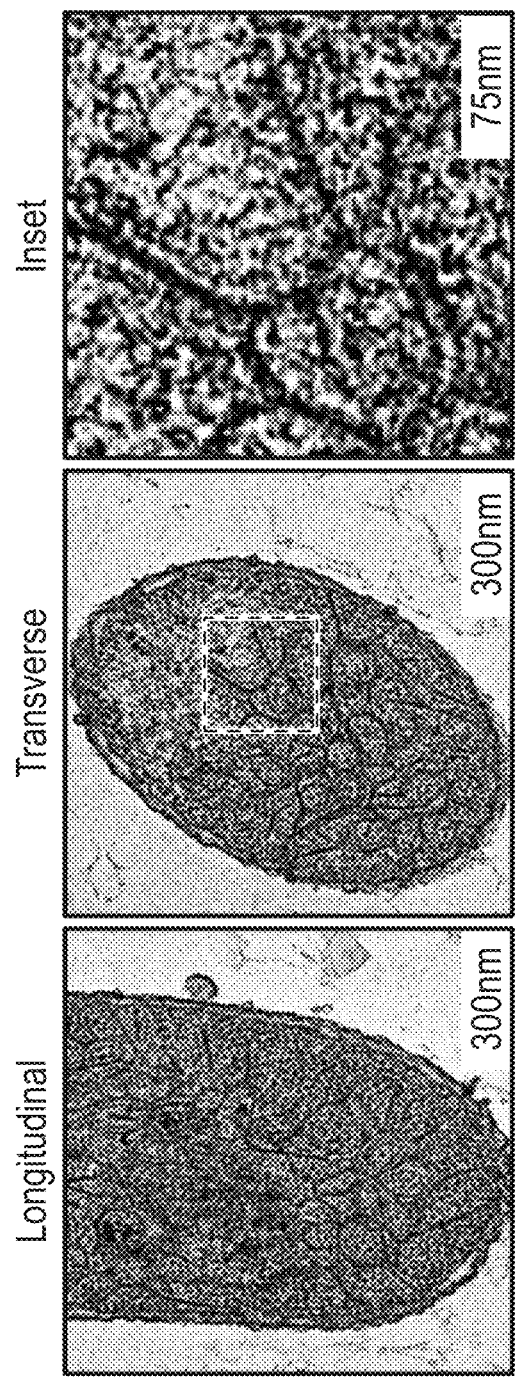
Figure 1E:
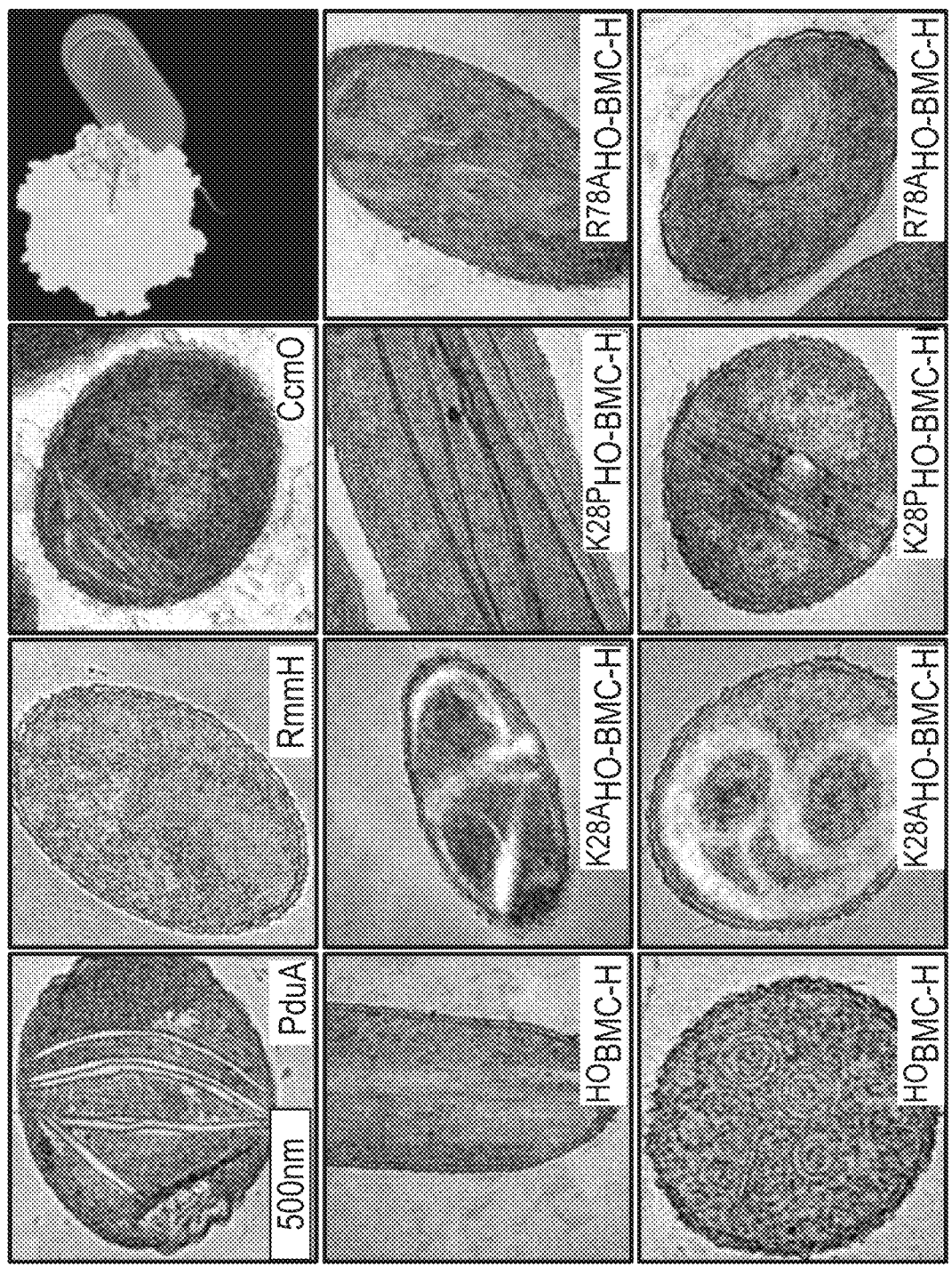
Figure 1F:
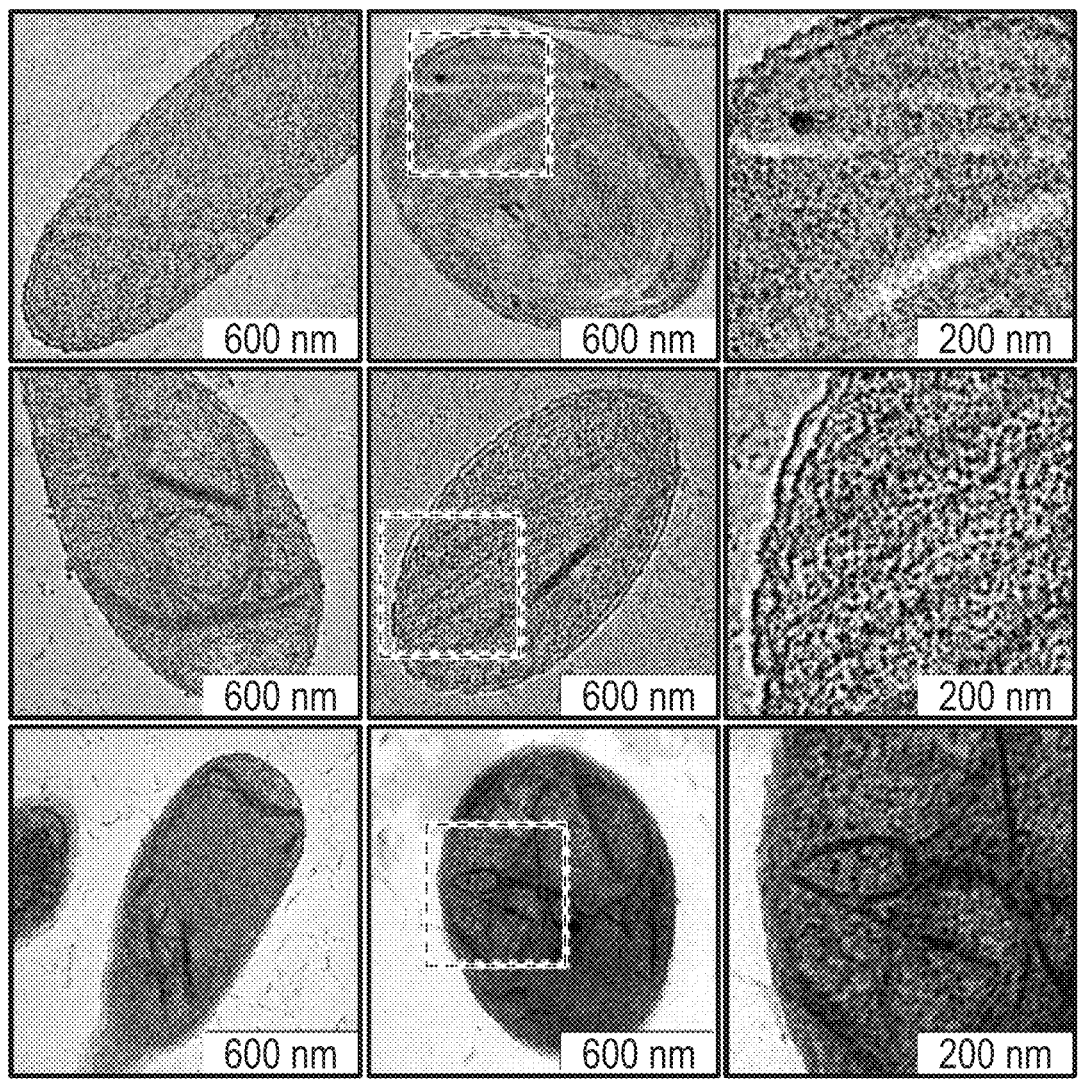

The unmodified HO BMC-H (WT-HO BMC-H 5815) formed protein sheets that frequently rolled in upon themselves to create characteristic "rosettes" (FIG. 1B). However, only amorphous electron dense regions with characteristics similar to protein inclusion bodies were observed following expression of HO BMC-H 5815 tagged with a Synthetic Zipper via a rigid linker (construct WT-HO BMC-H ppgSZ5), (FIG. 1C). Conversely. HO BMC-H Synthetic Zipper fusions with a flexible linker design (WT-HO BMC-H ggsSZ5) formed curved, sheet-like structures within the cytosol (FIG. 1D), apparently maintaining a higher-order arrangement similar to WT-HO BMC-H (FIG. 1B). The sheets formed by WT-HO BMC-H ggsSZ5 tended to pack in a less dense arrangement, appearing as a webwork of curls (FIG. 1B, 1D). Protein structure evaluation software suggested a high degree of steric clash could occur between the Synthetic Zipper (SZ) extensions when they were attached via a rigid linker. Hence, flexible linkers were used that were rich in glycine and serine residues.

For example, scaffold protein 5815 was designed to include at the C-terminus: a GGGGS linker (SEQ ID NO:7), a synthetic zipper with sequence NTVKELKNYI QELEER-NAELKNLKEHLKFAKAELEFELAAHKFE (SEQ ID NO:5; synthetic zipper 5), a PPG linker, and an YPYDVPDYA (SEQ ID NO:8) hemagglutinin (HA) tag. This linker-synthetic zipper-linker-HA fusion partner (referred to as Synthetic Zipper5) has the following sequence (SEQ ID NO:9) and can be linked to the C-terminus of a ScaFS domain.

```
              G GGGSNTVKEL KNYIQELEER
121 NAELKNLKEH LKFAKAELEF ELAAHKFEPP GYPYDVPDYA
```

The Scaffold protein 5815 construct therefore has the following C-terminal fusion partner: LINKER Synthetic Zipper5 LINKER HA Tag, which has the following sequence (SEQ ID NO:10).

```
  1 MADALGMIEV RGFVGMVEAA DAMVKAAKVE LIGYEKTGGG
 41 YVTAVVRGDV AAVKAATEAG QRAAERVGEV VAVEVIPRPH
 81 VNVDAALPLG RTPGMDKSAG GGGSNIVKEL KNYTQFLEER
121 NAELKNLKEH LKFAKAELFF ELAAHKTFPP GYPYDVPDYA
```

Additional ScaFs were made by modification of the wild type 5815 HO BMC-H ScaFs and then tagged with a Synthetic Zipper via the flexible-linker design. For example, a modified 5815 HO BMC-H domain with an alanine substitution at position 28 to replace the lysine (K28A). The sequence of this K28A 5815 ScaFs is shown below as SEQ ID NO:2 (with the substituted alanine highlighted in bold and with underlining).

```
  1 MADALGMIEV RGFVGMVEAA DAMVKAAAVE LIGYEKTGGG
 41 YVTAVVRGDV AAVKAATEAG QRAAERVGEV VAVEVIPRPH
 81 VNVDAALPLG RTPGMDKSA
```

When linked to Synthetic Zipper5, the K28A 5815-Synthetic Zipper5 construct has the following sequence (SEQ ID NO:11) (with the substituted alanine highlighted in bold and with underlining).

```
  1 MADALGMIEV RGFVGMVEAA DAMVKAAAVE LIGYFKIGGG
 41 YVTAVVRGDV AAVKAATEAG QRAAERVGEV VAVHVIPRPH
 81 VNVDAALPLG RTPGMDKSAG GGGSNTVKEL KNYIQELEER
121 NAELKNLKEH LKFAKAELEF ELAAHKFEPP GYPYDVPDYA
```

In another example, a modified 5815 HO BMC-H domain was made with a proline substitution at position 28 to replace the lysine (K28P). The sequence of this K28P 5815 ScaFs is shown below as SEQ ID NO:3 (with the substituted proline highlighted in bold and with underlining).

```
  1 MADALGMIEV RGFVGMVEAA DAMVKAAPVE LIGYEKTGGG
 41 YVTAVVRGDV AAVKAATEAG QRAAERVGEV VAVHVIPRPH
 81 VNVDAALPLG RTPGMDKSA
```

When linked to Synthetic Zipper5, the K28P 5815—Synthetic Zipper5 construct has the following sequence (SEQ ID NO:12) (with the substituted proline highlighted in bold and with underlining).

```
  1 MADALGMIEV RGFVGMVEAA DAMVKAAPVE LIGYEKTGGG
 41 YVTAVVRGDV AAVKAATEAG QRAAERVGEV VAVHVIPRPH
 81 VNVDAALPLG RTPGMDKSAG GGGSNIVKEL KNYIQELEER
121 NAELKNLKEH LKFAKAELEF ELAAHKFEPP GYPYDVPDYA
```

In another example, a modified 5815 HO BMC-H domain with an alanine substitution at position 78 to replace the arginine (R78A). The sequence of this R78A 5815 ScaFs is shown below as SEQ ID NO:4 (with the substituted alanine highlighted in bold and with underlining).

```
  1 MADALGMIEV RGFVGMVEAA DAMVKAARVE LIGYEKTGGG
 41 YVTAVVRGDV AAVKAATEAG QRAAERVGEV VAVEVIPAPH
 81 VNVDAALPLG RTPGMDKSA
```

When linked to Synthetic Zipper5, the R78A 5815—Synthetic Zipper5 construct has the following sequence (SEQ ID NO:13) (with the substituted alanine highlighted in bold and with underlining).

```
  1 MADALGMIEV RGFVGMVEAA DAMVKAAKVE LIGYEKTGGG
 41 YVTAVVRGDV AAVKAATEAG QRAAERVGEV VAVHVIPAPH
 81 VNVDAALPLG RTPGMDKSAG GGGSNTVKEL KNYIQELEER
121 NAELKNLKEH LKFAKAELEF ELAAHKFEPP GYPYDVPDYA
```

Each of the foregoing modified 5815 ScaFs—Synthetic Zipper5 constructs (with SEQ ID NOs:8, 10, and 12) formed higher-order assemblies in the cytosol of *E. coli* (FIG. 1E, 1F) that exhibited features similar to the parental ScaFs (i.e., those not modified with the appended Synthetic Zipper; FIG. 1E).

Example 3: Assembling Cargo Proteins onto 5815 ScaFs Using Synthetic Zipper Constructs This Example describes linkage of cargo proteins to the ScaFs-Synthetic Zipper constructs, and evaluation of such ScaFs-Synthetic Zipper-Cargo constructs to ascertain whether they can assemble with the scaffolding ScaFS proteins.

To examine whether cargo proteins linked to Synthetic Zipper domains were capable of specifically binding to the ScaFS proteins, fluorescent cargo protein were linked to the Synthetic Zipper 6 domain (SZ6). The Synthetic Zipper domain (SZ6) has the following sequence (SEQ ID NO:6).

```
  1 MQKVAQLKNR VAYKLKENAK LENIVARLEN DNANLEKDIA
 41 NLEKDIANLE RDVAR
```

The SZ6 domain was selected because it reportedly can form heterodimers with the Synthetic Zipper 5 domain (SZ5) with nanomolar affinity (Kd<15 nM)(Thompson et al., 2012).

Nucleic acids were constructed to encode the SZ6 domain linked to a fluorescent mNeonGreen or mScarlet-I cargo protein via a glycine-rich linker (GSGGGSGGGS, SEQ ID NO:14), where the mNeonGreen cargo protein had a C-terminal StrepII tag (SAWSHPQFEK, SEQ ID NO:15). The sequence of the mNeonGreen protein segment is shown below (SEQ ID NO:16).

```
  1  MVSKGEEDNM  ASLPATHELH  IFGSINGVDF  DMVGQGTGNP
 41  NDGYEELNLK  STKGDLQFSP  WILVPHIGYG  FHQYLPYPDG
 81  MSPFQAAMVD  GSGYQVHRTM  QFEDGASLTV  NYRYTYEGSH
121  IKGEAQVKGT  GFPADGPVMT  NSLTAADWCR  SKKTYPNDKT
161  IISTFKWSYT  TGNGKRYRST  ARTTYTFAKP  MAANYLKNQP
201  MYVFRKTELK  HSKTELNFKE  WQKAFTDVMG  MDELYK
```

The mScarlet-I protein segment has the following sequence (SEQ ID NO:17).

```
  1  MVSKGEAVIK  EFMRFKVHME  GSMNGHEFEI  EGEGEGRPYE
 41  GTQTAKLKVT  KGGPLPFSWD  ILSPQFMYGS  RAFIKHPADI
 81  PDYYKQSFPE  GFKWERVMNF  EDGGAVTVTQ  DTSLEDGTLI
121  YKVKLRGTNF  PPDGPVMQKK  TMGWEASTER  LYPEDGVLKG
161  DIKMALRLKD  GGRYLADFKT  TYKAKKPVQM  PGAYNVDRKL
201  DITSHNEDYT  VVEQYERSEG  RHSTGGMDEL  YK
```

The Synthetic Zipper6 LINKER mNeonGreen StrepII Tag construct has the following sequence (SEQ ID NO:18).

```
  1  MQKVAQLKNR  VAYKLKENAK  LENIVARLEN  DNANLEKDIA
 41  NLEKDIANLE  RDVARGSGGG  SGGGSMVSKG  EEDNMASLPA
 81  THELHIFGSI  NGVDFDMVGQ  GTGNPNDGYE  ELNLKSTKGD
121  LQFSPWILVP  HIGYGEHQYL  PYPDGMSPFQ  AAMVDGSGYQ
161  VHRTMQFEDG  ASLTVNYRYT  YEGSHIKGEA  QVKGTGFPAD
201  GPVMTNSLTA  ADWCRSKKTY  PNDKTIISTF  KWSYTTGNGK
241  RTRSTARTTY  TFAKPMAANY  LKNQPMYVFR  KTELKHSKTE
281  LNFKEWQKAF  TDVMGMDELY  KSAWSHPQFE  K
```

The Synthetic Zipper6 LINKER mScarlet-I StrepII Tag construct has the following sequence (SEQ ID NO:19).

```
  1  MQKVAQLKNR  VAYKLKENAK  LENIVARLEN  DNANLEKDIA
 41  NLEKDIANLE  RDVARGSGGG  SGGGSMVSKG  EAVIKEFMRF
 81  KVEMEGSMNG  HEFEIEGEGE  GRPYEGTQTA  KLKVTKGGPL
121  PFSWDILSPQ  FMYGSRAFIK  HPADIPDYYK  QSFPEGFKWE
161  RVMNFEDGGA  VTVTQDTSLE  DGTLIYKVKL  RGINFPPDGP
201  VMQKKTMGWE  ASTERLYPED  GVLKGDTKMA  LRLKDGGRYL
241  ADFKITYKAK  KPVQMRGAYN  VDRKLDITSH  NEDYTVVEQY
281  ERSEGRHSTG  GMDELYKSAW  SHPQFEK
```

Figure 2H:
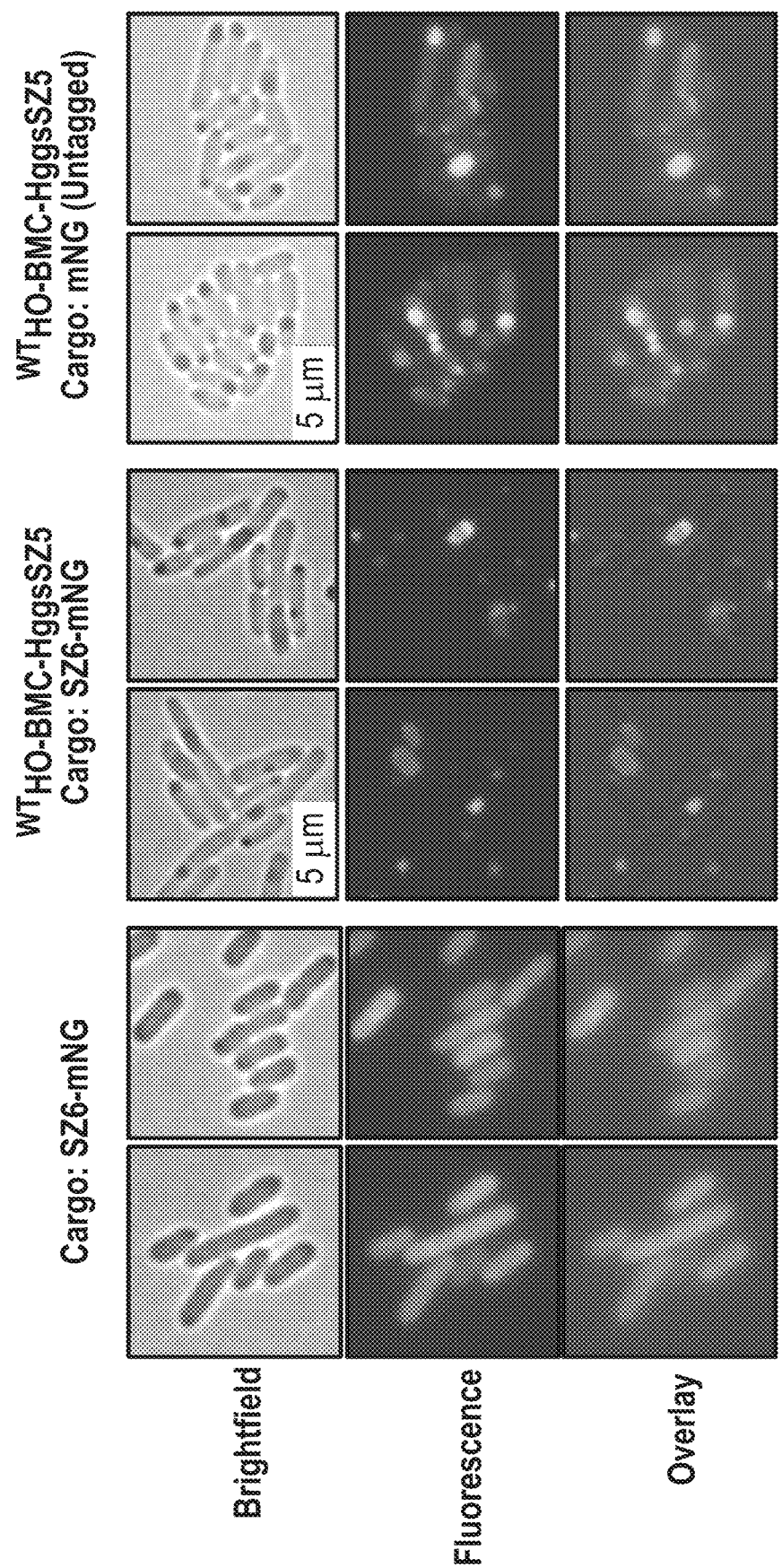

To evaluate scaffold assembly and dynamics intracellularly, initially only the Synthetic Zipper-fluorescent cargo proteins were expressed to load cells with freely diffusing fluorescent signal. After this delay, expression of SynZIP-BMC shell protein was then selectively turned on. Upon co-expression of the SZ6-reporter cargo and SZ5-ScaFS, successful assembly of the SZ5-ScaFS scaffold with the SZ6-reporter cargo protein was detected by observing fluorescence signals that localized to the vicinity of higher-order assemblies (FIG. 2A). As shown in FIG. 2H, a fluorescent reporter (mNeonGreen) exhibited more diffuse fluorescence in the cytosol of E. coli when expressed without the SZ6 tag that can bind the SZ5 tag on the SZ5-ScaFS scaffold, however when expressed with the SZ6 tag fluorescence was localized at discrete places in the cells because it could assemble with the SZ5-ScaFS scaffold. Hence, when co-expressed with a compatible ScaFS, the reporter strongly concentrated to punctate and filamentous structures within the cell (FIG. 2B-2D, 2H). The fluorescence signal was overlaid with cytosolic diffracting bodies that were observed in brightfield and that were consistent in shape and size to the protein sheets visualized by TEM (FIGS. 1, 2B, 2D and 2H). The higher resolution afforded by 3D-Structured Illumination Microscopy (SIM) further indicated that SZ6-tagged reporters form higher-order organizations similar to ScaFS assemblies viewed by TEM (FIGS. 2C-2D, 2H).

Unexpectedly, a negative control fluorescent reporter (i.e. a fluorescent protein lacking a cognate SZ domain) often concentrated near the diffracting bodies formed by overexpressed ScaFS (FIG. 2E), suggesting that ScaFS can interact with the fluorescent cargo protein without SZ5-SZ6 binding. In these instances, there was often a significant pool of cytosolic reporter (FIG. 2E), and the concentrated reporter pool appeared localized in the vicinity of, but not directly overlaid upon, the finer structural features of the underlying body. These subtle features were further highlighted by deconvolution of widefield images (FIG. 2E). In a co-immunoprecipitation assay only SZ6-tagged cargo was co-precipitated with purified SZ5-tagged ScaFS—untagged reporters did not demonstrate significant binding affinity. Taken together, the data show that untagged fluorescent cargo might be concentrated as a result of an artifact in vivo, rather than direct binding.

Other artifacts were observed that were associated with the expression of ScaFS from the strong T7 promoter, including decreased growth rate and distorted cellular morphologies (FIG. 2B-2E). Other works have also been reported over-expression and microcompartment-targeting anomalies in vivo (Liang et al., 2017; Lee, Mantell. Brown, et al., 2018).

Figure 2I:
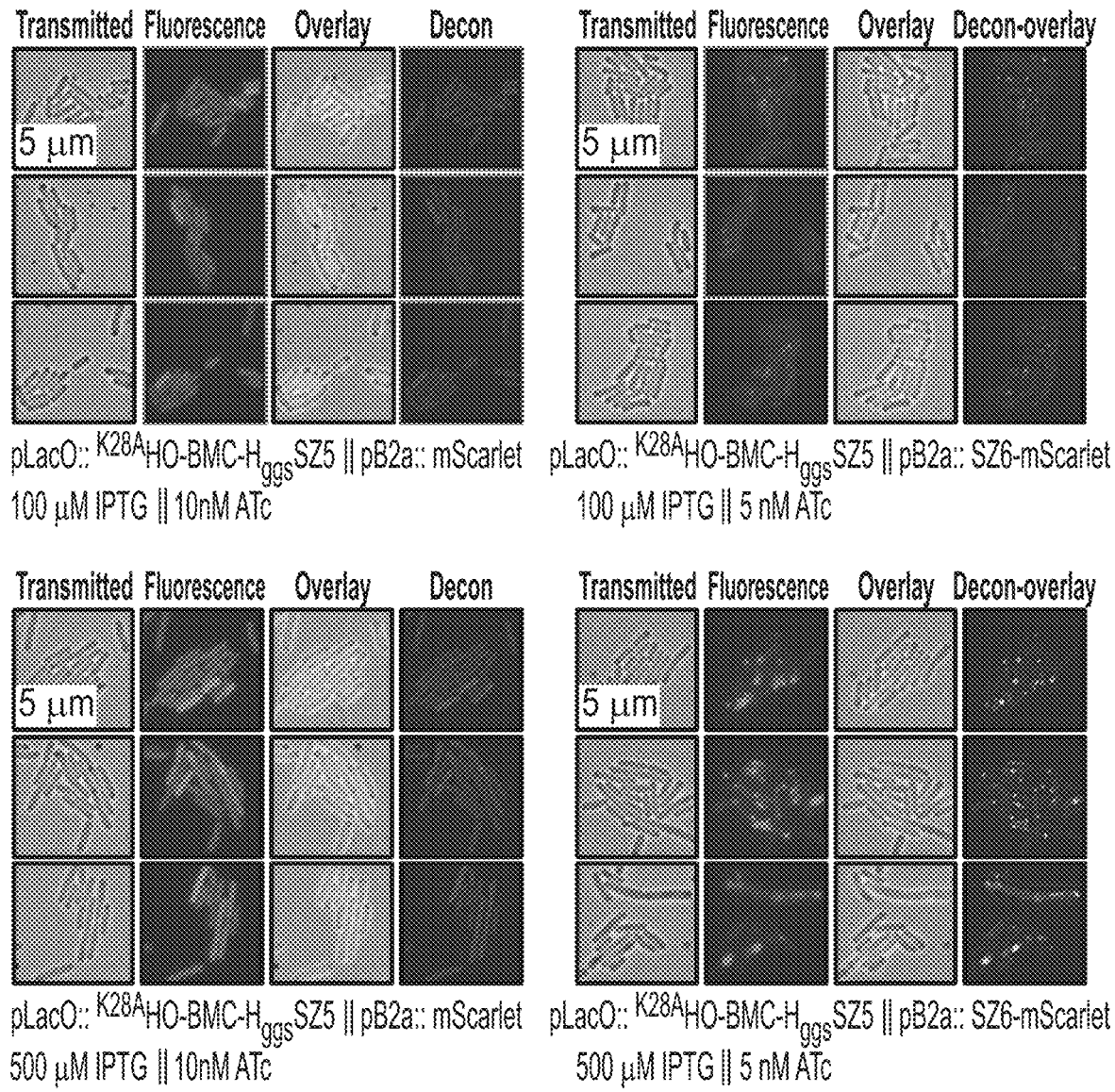

In view of the localization artifacts and cytotoxic effects observed when using a strong promoter to express ScaFS, the inventors decided to try using alternative, tunable promoters (Lee et al., 2011). E. coli cells expressing ScaFS via a tunable promoter retained normal morphology, and typically exhibited either no obvious internal diffracting bodies (low inducer concentration), or small punctate or filament-like diffractions (intermediate-to-high inducer concentrations; FIG. 2F-2G). When the ScaFS were co-expressed with two different SZ6-tagged fluorescent reporters, the fluorescent signal was concentrated strongly onto intracellular puncta and filaments (FIG. 2I). Furthermore, untagged fluorescent cargo (lacking the cognate SZ6 binding domain) remained delocalized throughout the cytosol when coexpressed with ScaFS under a low or moderate level of expression (FIG. 2I). Image error-mapping and super-resolution image processing (Gustafsson et al., 2016; Culley et al., 2018) (see Example 1. Materials and Methods) refined descriptions of fluorescent location. After processing, SZ-tagged fluorescent signal appeared in specific subcellular locations, while untagged cargo appeared diffuse (FIG. 2G-2I).

Figure 3A:
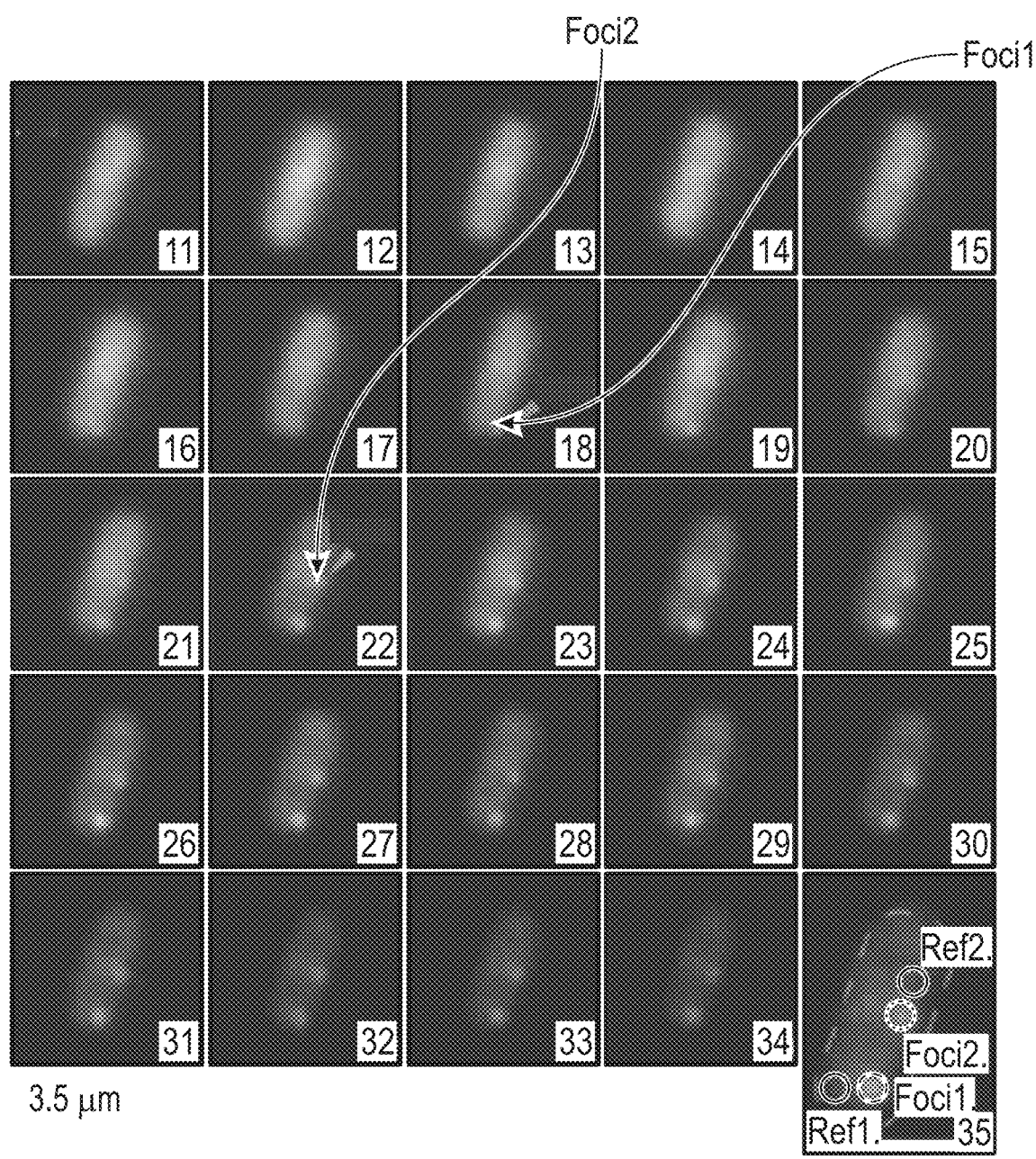
FIG. 3A-3D illustrate scaffold behavior by visualizing intracellular cargo dynamics.
Figure 3B:
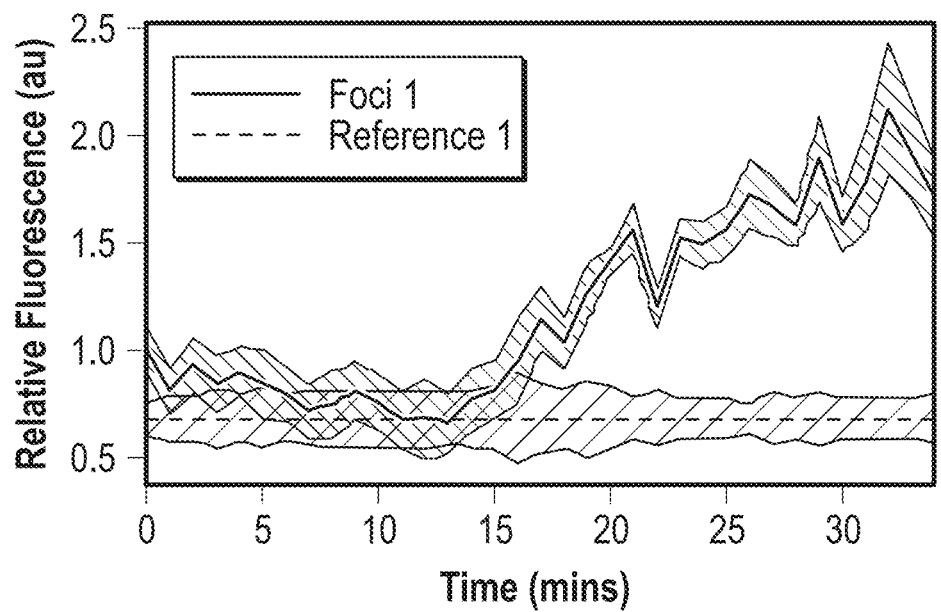
Figure 3B:
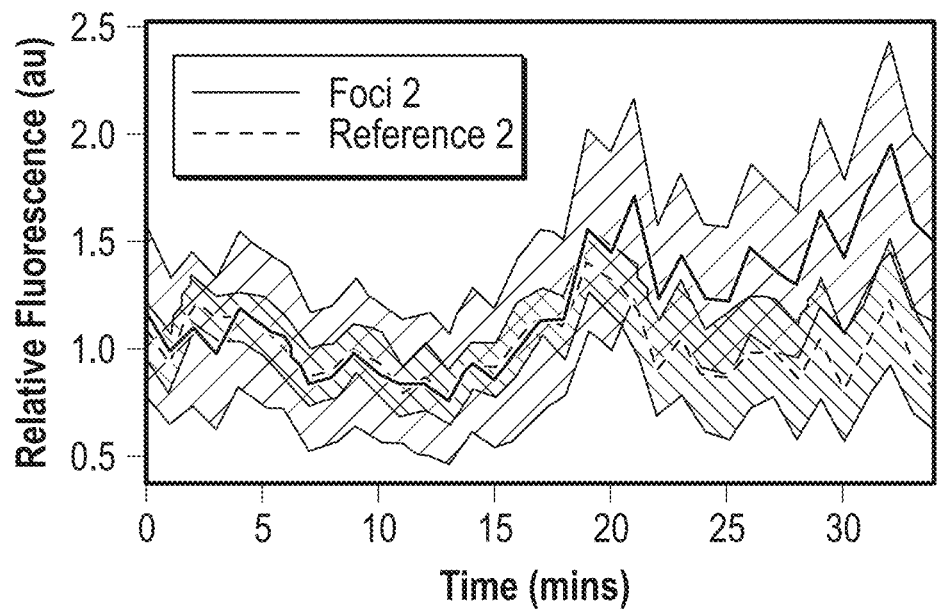
Figure 3C:
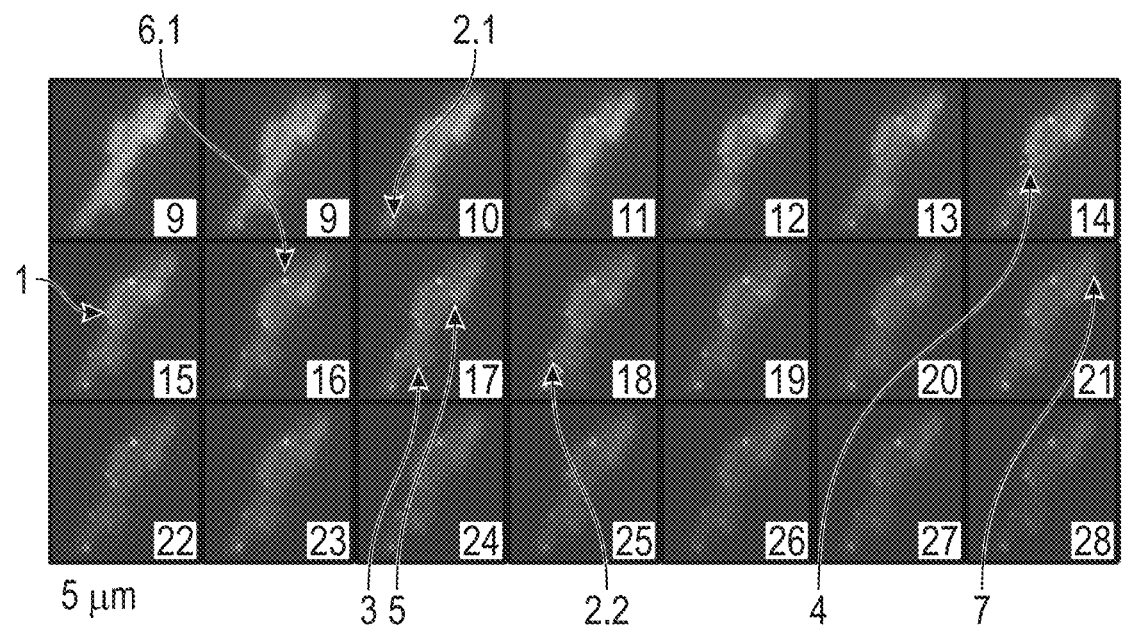

The dynamics of scaffold nucleation and maturation was then visualized over time in live cells. To accomplish this, expression of SZ6-mNG was induced for about 30 minutes to build a cytosolic pool of fluorescent cargo, then assembly was induced by expressing a compatible ScaFS (K28A-HO BMC-H ggsSZ5). Live-cell imaging revealed that cargo fluorescence initially appeared diffuse, but rapidly re-localized into intracellular puncta following ScaFS expression. At least one fluorescent focus site was evident in about 90% of cells within 60 minutes of ScaFS expression (n=31). Over the time-course, cargo continued to concentrate to subcellular domains in the cell, although the localization pattern at later time points increasingly resembled filaments rather than small puncta (2-18 hours). By contrast, untagged cargo exhibited a primarily diffuse localization throughout the cytosol, regardless of the length of time following induction. Three dimensional-total internal reflectance microscopy (3D-TIRFM) tracked fluorescent cargo protein location in individual cells with improved spatio-temporal resolution. This technique allowed observation of cargo clustering in small concentrated regions as early as about 10 minutes following ScaFS induction, which appeared to be nucleation events of scaffold assembly (FIG. 3A; white arrowhead). In the minutes immediately following a nucleation event, a rapid rise was frequently observed in the relative fluorescence of the puncta (FIG. 3A), although not all puncta exhibited identical kinetics. In some instances, the "maturation" appeared to stall even as a sister-foci within the cell continued to grow in size and/or intensity (FIG. 3B).

Figure 4A:
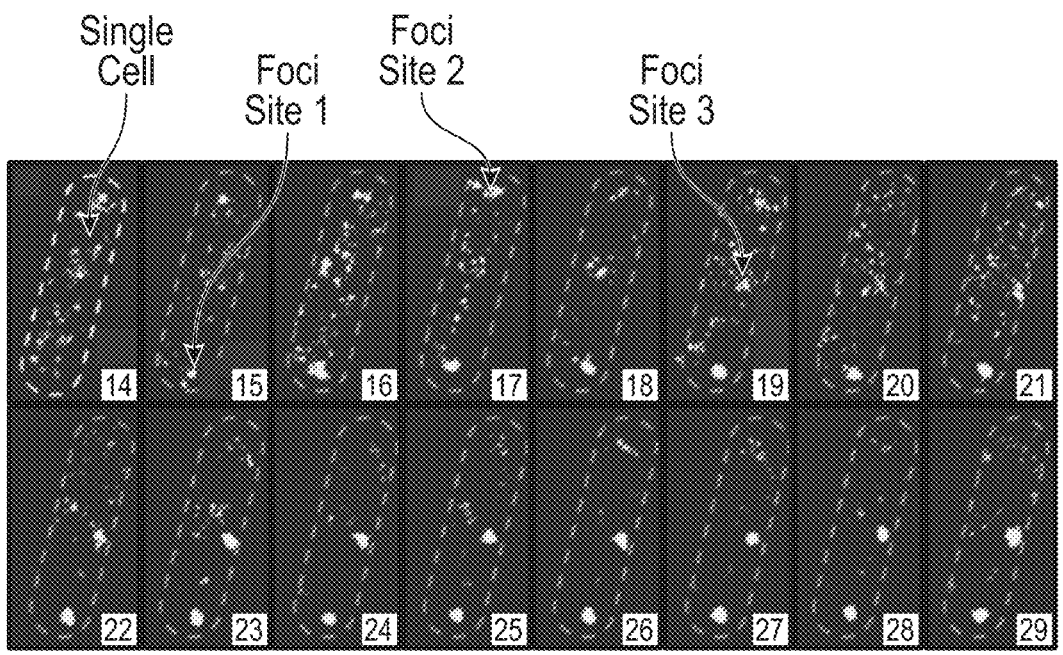
FIG. 4A-4E illustrates the diverse maturation fates of nucleated ScaFS.
Figure 4B:
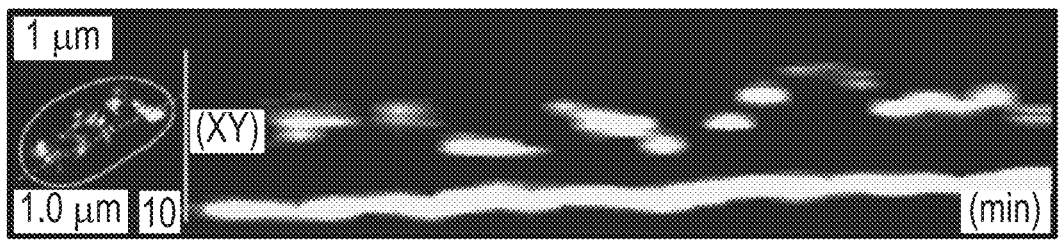
Figure 4C:
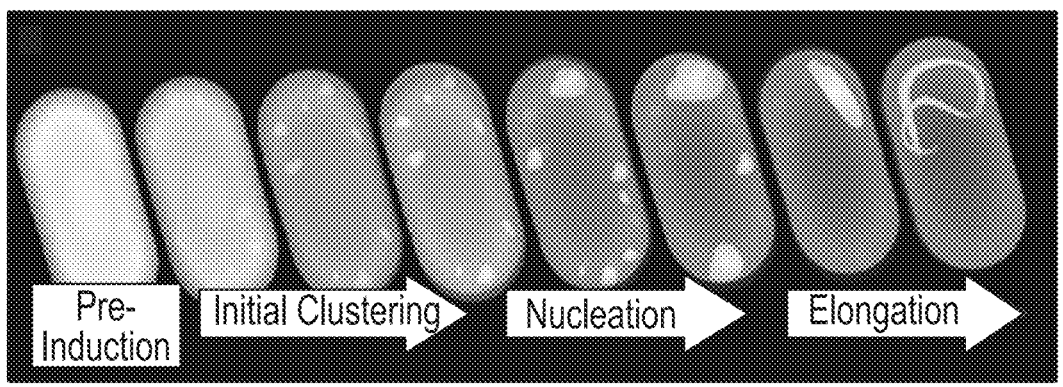
Figure 4D:
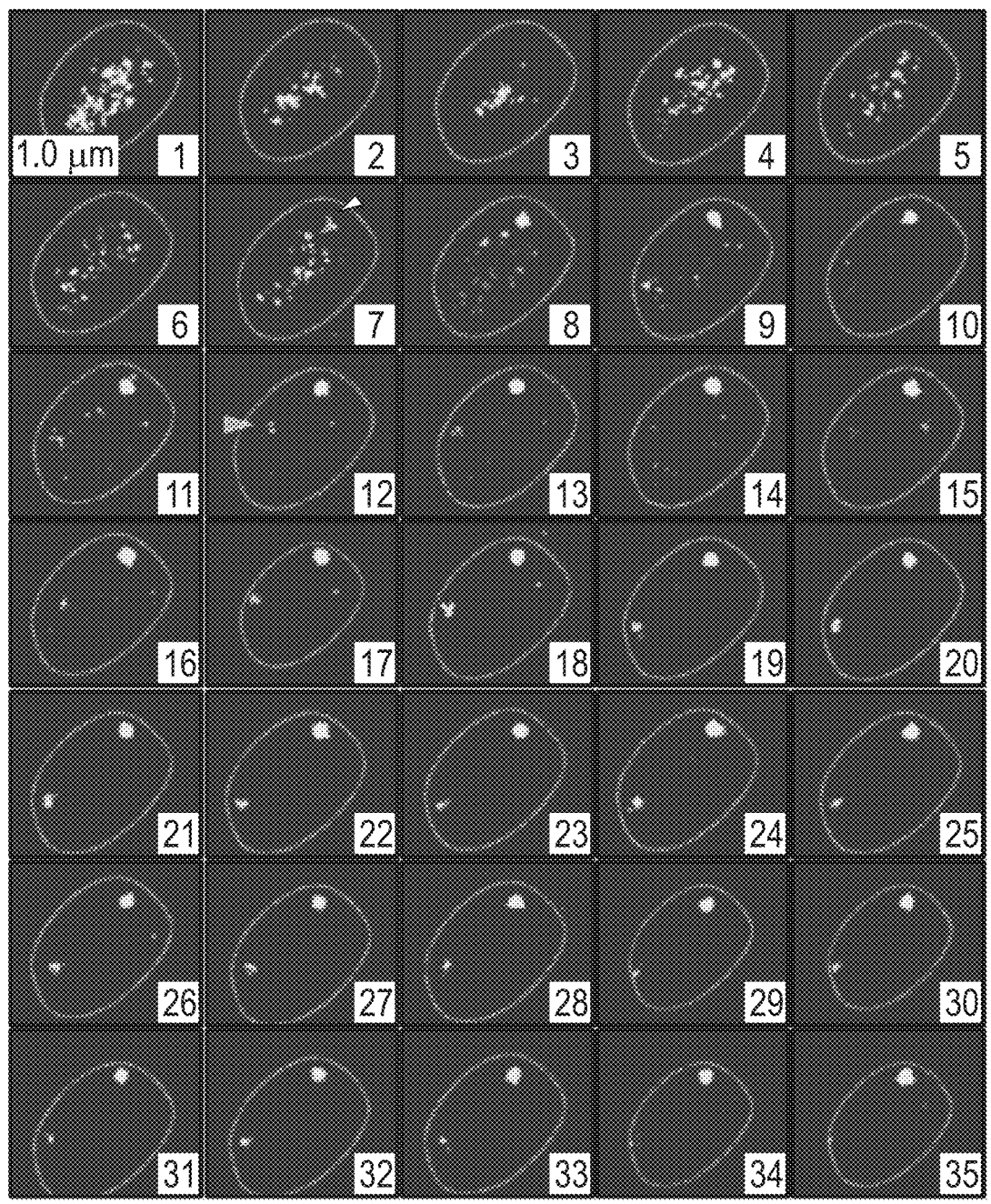
Figure 4E:
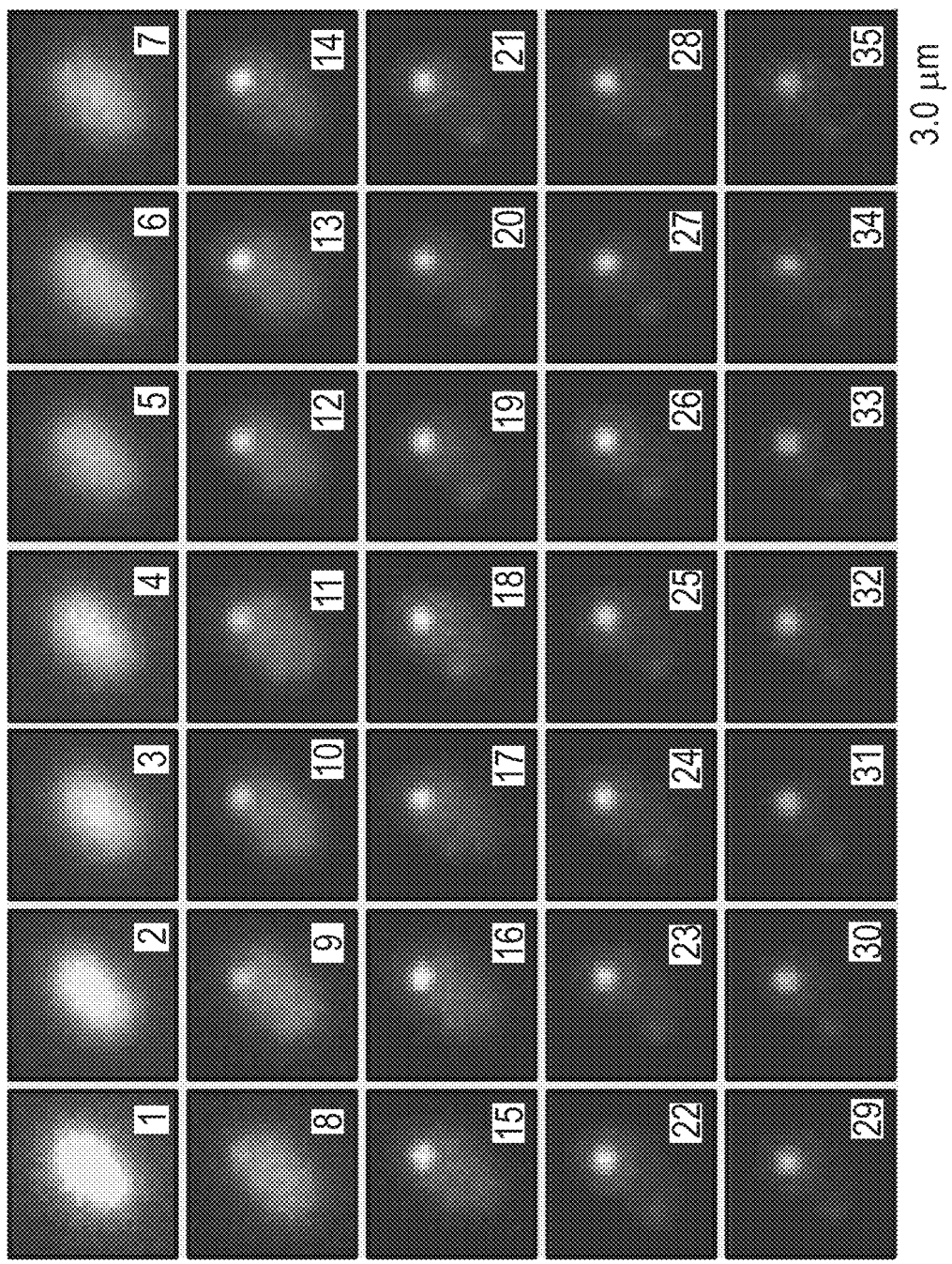

SRRF analysis of the early stages of nucleation suggested additional subtleties in dynamics. For example, persistent fluorescent foci were often detected via SRRF at time points earlier than they became resolved by conventional widefield imaging (FIG. 4A, 4D, 4E). Newly nucleated foci exhibited local movements while relatively little motion was observed with the larger "mature" cellular foci (FIG. 4B).

Figure 3D:
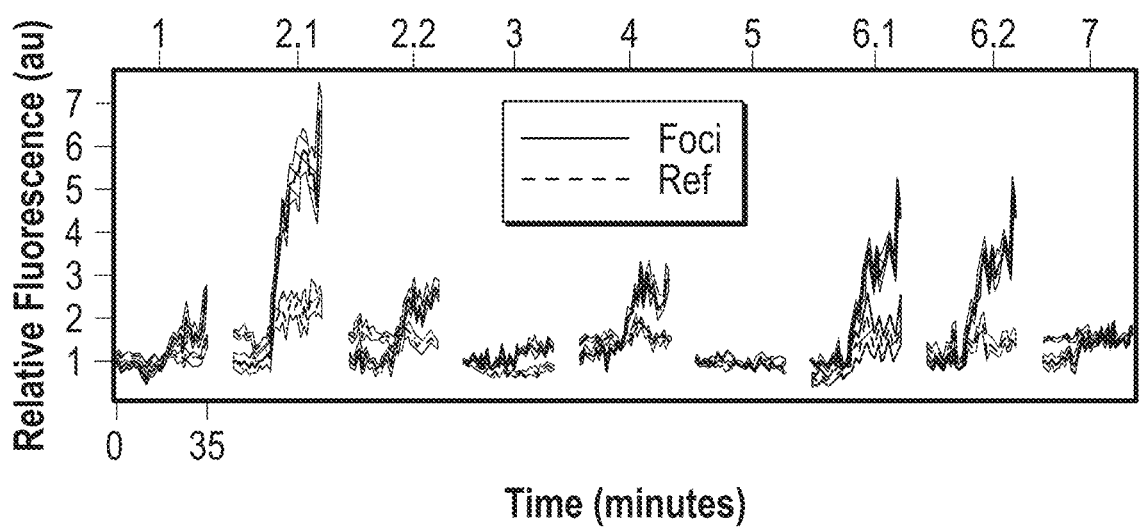

Multiple examples were captured where one focus decreased in size and intensity while another maintained size or became more prominent (FIG. 3D). Similarly, examples were observed where a small cluster of cargo could be detected at a given cellular position for minutes, but eventually diminish (FIG. 4A, 4D, 4E). These events were interpreted as nucleated ScaFS, but ones that fail to grow and instead become disassembled over time (FIG. 4A). Indeed, the nucleation of one or more assemblies at early time points typically was accompanied by a decrease in the background level of cargo (FIGS. 3-4), suggesting that the level of freely diffusible ScaFS appears depleted rapidly as nucleated scaffolds grow. Depletion of this free pool of ScaF subunits has implications for "competitive" behaviors between self-assembling systems that share the cytosol, with potential limitations on number and size of scaffolds that can be supported by a single cell.

REFERENCES

Agapakis. C. M., Boyle, P. M., and Silver. P. A. Natural strategies for the spatial optimization of metabolism in synthetic biology. *Nat. Chem. Biol.* 8: 527-535. (2012).

Bari. N. K., Kumar, G., Bhatt, A., Hazra, J. P., Garg, A., Ali. M. E., and Sinha, S. Nanoparticle fabrication on bacterial microcompartment surface for the development of hybrid enzyme-inorganic catalyst. *ACS Catal.* 8: 7742-7748. (2018).

Baek. M., Park. T., Heo. L., Park. C. & Seok, C. Galaxy-Homomer: a web server for protein homo-oligomer structure prediction from a monomer sequence or structure. *Nucleic Acids Res.* 45. W320-W324 (2017).

Bienick. M. S., Young, K. W., Klesmith, J. R., Detwiler. E. E., Tomek, K. J., and Whitehead, T. A. The interrelationship between promoter strength, gene expression, and growth rate. *PloS One* (2014).

Bindels, D. S. et al. mScarlet: a bright monomeric red fluorescent protein for cellular imaging. *Nature Publishing Group* 14, 53-56 (2017).

Castellana, M., Wilson. M. Z., Xu, Y., Joshi, P., Cristea, I. M., Rabinowitz, J. D., et al. Enzyme clustering accelerates processing of intermediates through metabolic channeling. *Nat. Biotechnol.* 32: 1011-1018. (2014).

Chen, R., Chen, Q., Kim. H., Siu, K. H., Sun, Q., Tsai, S. L., and Chen, W. Biomolecular scaffolds for enhanced signaling and catalytic efficiency. *Curr. Opin. Biotechnol.* 28: 59-68. (2014).

Chen. X., Zaro, J. L., and Shen. W. C. Fusion protein linkers: Property, design and functionality. *Adv. Drug Deliv. Rev.* 65: 1357-1369. (2013).

Culley. S., Albrecht, D., Jacobs, C., Pereira, P. M., Leterrier, C., Mercer, J., and Henriques, R. Quantitative mapping and minimization of super-resolution optical imaging artifacts. *Nat. Methods* 15: 263-266. (2018).

Delebecque, C. J., Lindner, A. B., Silver, P. A., and Aldaye, F. A. Organization of intracellular reactions with rationally designed RNA assemblies. *Science* (80). 333: 470-474 (2011).

Dueber, J. E., Wu. G. C., Malmirchegini, G. R., Moon, T. S., Petzold, C. J., Ullal, A. V, et al. Synthetic protein scaffolds provide modular control over metabolic flux. *Nat. Biotechnol.* 27: 753-759. (2009).

Falk, T., Mai, D., Bensch, R., Qigek, O., Abdulkadir, A., Marrakchi, Y., et al. U-Net: deep learning for cell counting, detection, and morphometry. *Nat. Methods* 16: 67-70. (2019).

Frederix, P. W. J. M., Patmanidis, I. & Marrink. S. J. Molecular simulations of self-assembling bio-inspired supramolecular systems and their connection to experiments. *Chem Soc Rev* 47, 3470-3489 (2018).

Giessen, T. W. and Silver, P. A. Encapsulation as a strategy for the design of biological compartmentalization. *J. Mol. Biol.* 428: 916-927. (2016).

Glover, D. J. and Clark. D. S. Protein calligraphy: A new concept begins to take shape. *ACS Cent. Sci.* 2: 438-444. (2016).

Good, M. C., Zalatan, J. G., and Lim. W. A. Scaffold Proteins: Hubs for controlling the flow of cellular information. *Science* (80). 332: 680-686. (2011).

Gustafsson. N., Ashdown, G., Owen, D., Pereira, P., Henriques, R., and Culley. S. Fast live-cell conventional fluorophore nanoscopy with ImageJ through super-resolution radial fluctuations. *Nature Communications* (2016).

Hagen, A., Kerfeld, C. In vitro assembly of engineered bacterial microcompartment shells enables encapsulation of diverse cargo. *Nano Letters* (2019).

Horn, A. H. C. and Sticht, H. Synthetic Protein scaffolds based on peptide motifs and cognate adaptor domains for improving metabolic productivity. *Front. Bioeng. Biotechnol.* (2015).

Huber. I. et al. Construction of recombinant pdu metabolosome shells for small molecule production in *Corynebacterium glutamicum*. *ACS Synth Biol* (2017).

Kafri, M., Metzl-Raz, E., Jona, G., and Barkai, N. The cost of protein production. *Cell Rep.* 14: 22-31. (2016).

Källberg. M. et al. Template-based protein structure modeling using the RaptorX web server. *Nat Protoc* 7, 1511-1522 (2012).

Kerfeld. C. A., Aussignargues, C., Zarzycki. J., Cai, F., and Sutter, M. Bacterial microcompartments. *Nat. Rev. Microbiol.* (2018).

Lassila. J. K., Bernstein. S. L., Kinney, J. N., Axen. S. D. & Kerfeld, C. A. Assembly of 1) robust bacterial microcompartment shells using building blocks from an organelle of unknown function. *Journal of Molecular Biology* 426, 2217-2228 (2014).

Lee. H., DeLoache. W. C., and Dueber, J. E. Spatial organization of enzymes for metabolic engineering. *Metab. Eng.* 14: 242-251. (2012).

Lee, M. J., Brown, I. R., Juodeikis, R., Frank, S., and Warren, M. J. Employing bacterial microcompartment technology to engineer a shell-free enzyme-aggregate for enhanced 1,2-propanediol production in *Escherichia coli*. *Metab. Eng.* 36: 48-56. (2016).

Lee, M. J., Mantell, J., Brown, I. R., Fletcher, J. M., Verkade, P., Pickersgill, R. W., et al. De novo targeting to the cytoplasmic and luminal side of bacterial microcompartments. *Nat Commun.* (2018).

Lee, M. J., Mantell, J., Hodgson, L., Alibhai, D., Fletcher, J. M., Brown, I. R., et al. Engineered synthetic scaffolds for organizing proteins within the bacterial cytoplasm. *Nat Chem. Biol.* 14: 142-147. (2018).

Lee, M. J., Palmer, D. J., and Warren, M. J. Biotechnological advances in bacterial microcompartment technology. *Trends Biotechnol.* 37: 325-336. (2019).

Lee, T., Krupa, R. A., Zhang, F., Hajimorad, M., Holtz, W. J., Prasad, N., et al. BglBrick vectors and datasheets: A synthetic biology platform for gene expression. *J. Biol. Eng.* 5: 12. (2011).

Liang, M., Frank, S., Lünsdorf, H., Warren, M. J., and Prentice, M. B. Bacterial microcompartment-directed polyphosphate kinase promotes stable polyphosphate accumulation in *E. coli*. *Biotechnol. J.* 12 (2011).

Lim, W. A. Designing customized cell signalling circuits. *Nat Rev. Mol. Cell Biol.* 11: 393-403. (2011).

Luo, Q., Hou, C., Bai, Y., Wang, R., and Liu, J. Protein assembly: versatile approaches to construct highly ordered nanostructures. *Chem. Rev.* 116: 13571-13632. (2016).

MacCready, J. S., Hakim, P., Young, E. J., Hu, L., Liu, J., Osteryoung, K. W., et al. Protein gradients on the nucleoid position the carbon-fixing organelles of cyanobacteria. *eLife* (2018).

Mahalik, J. P., Brown, K. A., Cheng, X., and Fuentes-Cabrera, M. Theoretical study of the initial stages of self-assembly of a carboxysome's facet. *ACS Nano* 10: 5751-5758. (2016).

Myhrvold, C., Polka, J. K., and Silver, P. A. Synthetic Lipid-containing scaffolds enhance production by colocalizing enzymes. *ACS Synth. Biol.* 5: 1396-1403. (2016).

Pugh, G. C., Burns, J. R. & Howorka, S. Comparing proteins and nucleic acids for next generation biomolecular engineering. *Nature Reviews Chemistry* 2018 2:7 2, 113-130 (2018).

Plegaria, J. S and Kerfeld, C. A. Engineering nanoreactors using bacterial microcompartment architectures. *Current Opinion in Biotechnology* 51:1-7. (2018).

Savage. D. F., Afonso, B., Chen, A. H., and Silver, P. A Spatially ordered dynamics of the bacterial carbon fixation machinery. *Science* 327: 1258-61. (2010).

Schindelin. J. et al. Fiji: an open-source platform for biological-image analysis. *Nature Publishing Group* 9, 676-682 (2012).

Schmidt-Dannert, S., Zhang. G., Johnston, T., Quin. M. B., and Schmidt-Dannert, C. Building a toolbox of protein scaffolds for future immobilization of biocatalysts. *Appl. Microbiol. Biotechnol.* 102: 8373-8388. (2018).

Shaner. N. C. et al. A bright monomeric green fluorescent protein derived from Branchiostoma *lanceolatum*. *Nat Meth* 10, 407-409 (2013).

Siu, K. H., Chen. R. P., Sun. Q., Chen, L., Tsai, S. L., and Chen. W. Synthetic scaffolds for pathway enhancement. *Curr. Opin. Biotechnol.* 36: 98-106. (2015).

Streets, A. M. and Quake, S. R. Ostwald ripening of clusters during protein crystallization. *Phys. Rev. Lett.* 104 (2010).

Sutter. M., McGuire. S., Ferlez. B., and Kerfeld, C. A. Structural characterization of a synthetic tandem-domain bacterial microcompartment shell protein capable of forming icosahedral shell assemblies. *ACS Synth. Biol.* 8: 668-674. (2019).

Thompson, K. E., Bashor. C. J., Lim, W. A., and Keating. A. E. Synzip protein interaction toolbox: In vitro and in vivo specifications of heterospecific coiled-coil interaction domains. *ACS Synth. Biol.* 1: 118-129. (2012).

Wang, Y., Heermann, R., and Jung, K. CipA and CipB as scaffolds to organize proteins into crystalline inclusions. *ACS Synth. Biol.* 6: 826-836. (2017).

Wheeldon, I., Minteer, S. D., Banta, S., Barton, S. C., Atanassov, P., and Sigman, M. Substrate channeling as an approach to cascade reactions. *Nat. Chen.* 8: 299-309. (2016).

Whitaker. W. R. and Dueber, J. E. Metabolic pathway flux enhancement by synthetic protein scaffolding. *Methods Enzymol.* 497: 447-468. (2011).

Xu, M., Singla. J., Tocheva. E. I., Chang, Y. W., Stevens, R. C., Jensen. G. J., and Alber. F. De Novo structural pattern mining in cellular electron cryotomograms. Structure 27: 679-691 (20193).

Young, E. J., Burton, R., Mahalik, J. P., Sumpter, B. G., Fuentes-Cabrera, M., Kerfeld. C. A., and Ducat, D. C. Engineering the bacterial microcompartment domain for molecular scaffolding applications. *Front. Microbiol.* (2017).

Zhang. G., Quin, M. B., and Schmidt-Dannert, C. Self-assembling protein scaffold system for easy in vitro coimmobilization of biocatalytic cascade enzymes. *ACS Catal.* 8: 5611-5620. (2018).

Ziatdinov. M., Dyck. O., Maksov. A., Li. X., Sang. X., Xiao, K., et al. Deep learning of atomically resolved scanning transmission electron microscopy images: chemical identification and tracking local transformations. *ACS Nano* 11: 12742-12752. (2017).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description provided in the specification and figures.

Statements:
1. A fusion protein comprising (a) a pfam00936 domain (ScaF) linked to a first synthetic zipper domain via a flexible peptide linker; or (b) a cargo protein linked to a second synthetic zipper domain via a flexible linker.
2. The fusion protein of statement 1, wherein the flexible peptide linker is a 3 to 20 amino acid peptide, with at least 60%, at least 70%, at least 80%, at least 90%, or at least 95% glycine residues, serine residues, or a combination of glycine and serine residues.
3. The fusion protein of statement 1 or 2, wherein the pfam00936 domain has a sequence with at least 90%, or at least 95% sequence identity to any of SEQ ID NO:1-4.
4. The fusion protein of statement 1, 2, or 3, wherein the first synthetic zipper and the second synthetic zipper bind noncovalently together.
5. The fusion protein of statement 1-3 or 4, wherein the first synthetic zipper has a sequence with at least 90%, or at least 95% sequence identity to SEQ ID NO:5 or 6, and wherein the second synthetic zipper binds to the first synthetic zipper.
6. The fusion protein of statement 1-4 or 5, wherein the pfam00936 domain (ScaF), the cargo protein, or a combination thereof each have a covalently linked marker.
7. The fusion protein of statement 1-5 or 6, wherein the cargo protein is a fluorescent protein, an enzyme, or a combination thereof.
8. The fusion protein of statement 1-6 or 7, wherein the first synthetic zipper, the second synthetic zipper, or a combination thereof each have a covalently linked marker.
9. The fusion protein of statement 7 or 8, wherein the marker(s) are selected from an epitope tag, a fluorescent protein, or a binding partner.
10. The fusion protein of statement 9, wherein the epitope tag or the binding protein binds to a binder entity so the pfam00936 domain (ScaF), the cargo protein, or the Synthetic Zipper can be detected or precipitated from a mixture.
11. The fusion protein of statement 9, wherein the epitope tag or the binding protein is a hemagglutinin (HA) tag, a StrepII epitope tag, or a histidine tag.
12. The fusion protein of statement 7-10 or 11, wherein the fluorescent protein is mNeonGreen, mScarlet-I, mMaple3, and the like.
13. A complex comprising (a) a pfam00936 domain (ScaF) linked to a first synthetic zipper domain via a flexible peptide linker; and (b) a cargo protein linked to a second synthetic zipper domain via a flexible linker.
14. The complex of statement 13, wherein the flexible peptide linker is a 3 to 20 amino acid peptide, with at least 60%, at least 70%, at least 80%, at least 90%, or at least 95% glycine residues, serine residues, or a combination of glycine and serine residues.
15. The complex of statement 13 or 14, wherein the pfam00936 domain has a sequence with at least 90%, or at least 95% sequence identity to any of SEQ ID NO:1-4.
16. The complex of any one of statements 13-15, wherein the first synthetic zipper and the second synthetic zipper bind noncovalently together.
17. The complex of any one of statements 13-16, wherein the first synthetic zipper has a sequence with at least 90%, or at least 95% sequence identity to SEQ ID NO:5 or 6, and wherein the second synthetic zipper binds to the first synthetic zipper.
18. The complex of any one of statements 13-17, wherein the pfam00936 domain (ScaF), the cargo protein, or a combination thereof each have a covalently linked marker.
19. The complex of any one of statements 13-18, wherein the cargo protein is a fluorescent protein, an enzyme, or a combination thereof.
20. The complex of any one of statements 13-19, wherein the first synthetic zipper, the second synthetic zipper, or a combination thereof each have a covalently linked marker.
21. The complex of any one of statements 13-20, wherein the marker(s) are selected from an epitope tag, a fluorescent protein, or a binding partner.
22. The complex of any one of statements 21, wherein the epitope tag or the binding protein binds to a binder entity so the pfam00936 domain (ScaF), the cargo protein, or the Synthetic Zipper can be detected or precipitated from a mixture.
23. The complex of any one of statements 21, wherein the epitope tag or the binding protein is a hemagglutinin (HA) tag, a StrepII epitope tag, or a histidine tag.
24. The complex of any one of statements 21-23, wherein the fluorescent protein is mNeonGreen, mScarlet-I, mMaple3, and the like.
25. An expression system comprising one or more expression cassettes, each expression cassette comprising a promoter operably linked to a nucleic acid segment encoding one or more of the fusion proteins of any of statements 1-12.
26. The expression system of statement 25, comprising a first expression cassette comprising a promoter operably linked to a nucleic acid segment encoding one or more pfam00936 domain (ScaF), each pfam00936 domain (ScaF) linked or fused to a first synthetic zipper domain via a flexible peptide linker; and a second expression cassette comprising a promoter operably linked one or more cargo protein, each cargo protein linked or fused to a second synthetic zipper domain via a flexible linker.
27. The expression system of statement 25 or 26, wherein the first expression cassette promoter, the second expression cassette promoter, or both are tunable promoters or inducible promoters.
28. The expression system of statement 27, wherein one or more of the tunable promoters or the inducible promoters comprise tetracycline-regulated promoters, propionate-regulated promoters, arabinose-inducible promoters, propionate-inducible promoters, lactose-inducible promoters, or IPTG-inducible promoters.
29. The expression system of statement 27 or 28, wherein one or more of the tunable promoters or the inducible promoters comprise Ptet, tetR. PprpB, prpR. PBAD, or araC promoters.
30. The expression system of any one of statements 25-29, comprising one or more expression vectors, each expression vector comprising at least one of the expression cassettes.
31. An in vitro system comprising the expression system of any one of statements 25-30 and transcription (RNA polymerase) and translation (ribosomal) proteins for synthesizing RNA and synthesizing protein.
32. The in vitro system of statement 31, comprising extracts of bacterial cytoplasm.

33. A host cell comprising a pfam00936 domain (ScaF) linked to a first synthetic zipper domain via a flexible peptide linker.
34. The host cell of statement 32, further comprising a cargo protein linked to a second synthetic zipper domain via a flexible linker.
35. A host cell comprising the expression system of any one of statements 25-30.
36. The host cell of any one of statements 33-35, which is a prokaryotic cell.
37. The host cell of any one of statements 33-35, which is a eukaryotic cell.
38. The host cell of any one of statements 33-35, which is a bacterial cell or a cyanobacterial cell.
39. The host cell of any one of statements 33-35, which is a yeast cell.
40. A method comprising transforming a host cell with the expression system of any one of statements 25-30.
41. The method of statement 40, further comprising monitoring assembly of a complex comprising a pfam00936 domain (ScaF) within the cell.
42. The method of statement 40 or 41, further comprising monitoring localization of a signal generated by at least one cargo protein that complexes with the pfam00936 domain (ScaF).
43. The method of any one of statements 40-42, further comprising refining imaging of the assembly, complex, or of the signal within the cell.
44. The method of any one of statements 40-43, wherein monitoring assembly of the complex or monitoring localization of the signal comprises live cell imaging, light microscopy, error minimization, deconvolved localization pattern imaging, enhanced image deconvolution, enhanced image radial fluctuation, Super-Resolution Radial Fluctuations (SRRF)-processed fluorescence imaging, transmission electron microscopy (TEM), three-dimensional Secondary Ion Mass Spectrometry (3D-SIM), time lapse photography, image alignment, compiling total internal reflectance photomicrograph frames, compiling structured illumination microscopy Z-stack photomicrograph frames, reference comparison, or a combination thereof.
45. A kit comprising: a first receptacle containing a first expression cassette or vector comprising a promoter operably linked to a nucleic acid segment encoding one or more pfam00936 domain (ScaF) fused to a first synthetic zipper domain via a flexible linker; a second receptacle comprising a second expression cassette or vector comprising a promoter operably linked to a site for insertion of a nucleic acid segment encoding one or more cargo protein, fused in frame to a segment encoding a flexible linker fused to second synthetic zipper domain; or a combination of the first receptacle and the second receptacle; and instructions for use thereof.
46. A kit, comprising the expression system of any one of statements 25-30, and instructions for use thereof.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A self-assembling protein comprising (a) a first fusion protein comprising a pfam00936 domain of Scaffolds Formed by BMC-Shell proteins (ScaF) linked to a first synthetic zipper domain via a flexible peptide linker, wherein the pfam00936 domain has an amino acid sequence with at least 90% sequence identity to any of SEQ ID NO:1-4; and (b) a second fusion protein comprising a second synthetic zipper domain linked to a flexible linker, wherein:
the first synthetic zipper domain and the second synthetic zipper domain are coiled-coil protein domains that noncovalently bind together to form a heterodimer; and
the flexible linker is configured to link to a cargo protein and the flexible linker comprises at least 60% glycine residues, serine residues, or a combination of glycine and serine residues.

2. The self-assembling protein of claim 1, wherein the flexible peptide linker is a 3 to 20 amino acid peptide.

3. The self-assembling protein of claim 1, wherein the first synthetic zipper has an amino acid sequence with at least 90% sequence identity to one of SEQ ID NO:5 or 6, and wherein the second synthetic zipper has an amino acid sequence with at least 90% sequence identity to the other of SEQ ID NO:5 or 6 and binds to the first synthetic zipper.

4. The self-assembling protein of claim 1, wherein the pfam00936 domain (ScaF), the cargo protein, or a combination thereof each have a covalently linked marker or reporter.

5. A self-assembling protein comprising:
(a) a pfam00936 domain of Scaffolds Formed by BMC-Shell proteins (ScaF) linked to a first synthetic zipper domain via a flexible peptide linker, wherein the pfam00936 domain has an amino acid sequence with at least 90% sequence identity to any of SEQ ID NO:1-4 and the first synthetic zipper domain has an amino acid sequence with at least 90% sequence identity to either of SEQ ID NO:5 or 6; and (b) a cargo protein linked to a second synthetic zipper domain via a flexible linker, wherein the second synthetic zipper has an amino acid sequence with at least 90% sequence identity to the other of SEQ ID NO:5 or 6, wherein the flexible linker comprises at least 60% glycine residues, serine residues, or a combination of glycine and serine residues.

6. The self-assembling protein of claim 5, wherein the flexible peptide linker is a 3 to 20 amino acid peptide.

7. The self-assembling protein of claim 1, wherein the at least one of the cargo proteins is a fluorescent protein.

* * * * *